US010793850B2

(12) United States Patent
Wiessenhaan et al.

(10) Patent No.: US 10,793,850 B2
(45) Date of Patent: *Oct. 6, 2020

(54) RECOMBINATION SYSTEM

(71) Applicant: DSM IP ASSETS B.V., Heerlen (NL)

(72) Inventors: Nathalie Wiessenhaan, Echt (NL);
Catharina Petronella Antonia Maria Kolen, Echt (NL); Bernard Meijrink, Echt (NL); Viktor Marius Boer, Echt (NL); Johannes Andries Roubos, Echt (NL); Yvonne Johannes Odilia Arendsen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 702 days.

This patent is subject to a terminal disclaimer.

(21) Appl. No.: 14/384,192

(22) PCT Filed: Mar. 12, 2013

(86) PCT No.: PCT/EP2013/055047
§ 371 (c)(1),
(2) Date: Sep. 10, 2014

(87) PCT Pub. No.: WO2013/135728
PCT Pub. Date: Sep. 19, 2013

(65) Prior Publication Data
US 2015/0037892 A1 Feb. 5, 2015

(30) Foreign Application Priority Data

Mar. 12, 2012 (EP) .................... 12159094

(51) Int. Cl.
C12N 15/90 (2006.01)
C12N 15/10 (2006.01)

(52) U.S. Cl.
CPC ......... C12N 15/102 (2013.01); C12N 15/902 (2013.01); *C12N 2800/30* (2013.01)

(58) Field of Classification Search
CPC .................................................. C12N 15/902
See application file for complete search history.

(56) References Cited

U.S. PATENT DOCUMENTS

| 2003/0199037 A1 | 10/2003 | Harris et al. |
| 2003/0233675 A1 | 12/2003 | Cao et al. |
| 2008/0085535 A1 | 4/2008 | Breuner et al. |

FOREIGN PATENT DOCUMENTS

| JP | 2005-176602 A | 7/2005 |
| WO | 2012/123429 A1 | 9/2012 |

OTHER PUBLICATIONS

You et al. (2009, Arch Microbiol, vol. 191, pp. 615-622.*
Sauer et al. (1988, PNAS, vol. 85, pp. 5166-5170).*

Kolb et al., "Insertion of a foreign gene into the ß-casein locus by Cre-mediated site-specofoc recombination." Gene 227 (1999) 21-31.
Barascu et al., "Homologous Recombination in Mammals." 23 Topics in Current Genetics (2013) 91-120.
Capecchi, "Gene targeting in mice: functional analysis of the mammalian genome for the twenty-first century" 6 Nature Reviews (2005) 507-512.
Hartmann et al., Validation of a Self-Excising Marker in the Human Pathogen Aspergillus fumigatus by Employing the ß-Rec/six Site-Specific Recombination System.: 76(18) Applied and Environmental Microbiology (2010) 6313-6317.
Cheng et al., "Controlling gene expression in yeast by inducible site-specific recombination." Nucleic Acids Research e108 (2000) 1-6.
International Search Report dated Jun. 14, 2013, issued in PCT/EP2013/055048.
Sauer, "Functional Expression of the cre-lox Site-Specific Recombination System in the Yeast *Saccharomyces cerevisiae*." Molecular and Cellu.
Waters et al., "Talaromyces emersonii Thermostable Enzyme Systems and Their Applications in Wheat Baking Systems." Journal of Agricultural and Food Chemistry, 2010, vol. 58, pp. 7415-7422.
Fairhead et al., "New Vectors for Combinatorial Deletions in Yeast Chromosomes and for Gap-repair Cloning using Split-marker Recombination." Yeast, 1996, vol. 12, pp. 1439-1457.
International Search Report received in corresponding PCT/EP2013/055051, dated Jul. 4, 2013.
Houbraken et al., A new genus comprising thermotolerant and thermophilicandspecies, Antonie Van Leeuwenhoek. Kluwer Academic Publishers. DO, vol. 101, No. 2, Oct. 2, 2011 (Oct. 2, 2011), pp. 403-421, XP03500386.
Heinzelman et al: "Efficient screening of fungal cellobiohydrolase class I enzymes for thermostabilizing sequence blocks by SCHEMA structure-guided recombination", protein Engineering, Design & Selection, Sep. 16, 2010 (Sep. 16, 2010), pp. 871-880, XP055045668.
Database, UniProt, Mar. 3, 2009 (Mar. 3, 2009), "SubName: Full=DNA repair protein Rad50;" XP002699061, retrieved from EBI accession No. UN I PROT:B8LXJ 1, Database accession No. B8LXJ1.
Database UniProt [Online], Mar. 3, 2009 (Mar. 3, 2009), "SubName: Full=DSB repair complex subunit Ku70, putative;", XP002699062, retrieved from EBI accession No. UNIPROT:B8MR17, Database accession No. B8MR17.
Database UniProt [Online], May 31, 2011 (May 31, 2011), "SubName: Full=Meiotic recombination protein dmc1;", XP002699063, retrieved from EBI accession No. UNIPROT:F2THH5, Database accession No. F2THH5.
Jain et al., "Development of a transformation system for the thermophilic fungus *Talaromyces* sp. CL240 based on the use of phleomycin resistamce as a dominant selectable marker." Mol Gen Genet (1992) 234: 489-493.
Murray et al., "Isolation of the glucose oxidase gene from Talaromyces flavus and characterisation of its role in the biocontrol of Verticillium dahliae." Curr Genet (1997) 32: 367-375.

(Continued)

Primary Examiner — Thaian N. Ton
Assistant Examiner — David A. Montanari
(74) Attorney, Agent, or Firm — McBee Moore & Vanik IP, LLC

(57) ABSTRACT

The present invention relates to a method for carrying out recombination at a target locus.

15 Claims, 7 Drawing Sheets
Specification includes a Sequence Listing.

(56) References Cited

OTHER PUBLICATIONS

International Search Report from corresponding PCT/EP2013/055047, dated Apr. 26, 2013.
Kolb, "Selection-Marker-Free Modification of the Murine [beta]-Casein Gene Using a 1 ox2722 Site", Analytical Biochemistry, vol. 290, No. 2, Mar. 1, 2001 (Mar. 1, 2001), pp. 260-271, XP055033798.
Cherepanov et al., "Gene disruption in *Escherichia coli*: Tc<R> and Km<R>cassettes with the option of Flp-catalyzed excision of the antibiotic-resistance determinant", Gene. Elsevier. Amsterdam. NL, vol. 1, 158, No. 1, Jan. 1, 1995 (Jan. 1, 1995). pp. 9-14, XP004206666.
You et al., "Gene-specific disruption in the filamentous fungus Cercospora nicotianae using a split-marker approach", Archives of Microbiology. Springer, Berlin, DE, vol. 191, No. 7, Jun. 9, 2009, (Jun. 9, 2009), pp. 615-622. XP019701743.
Uemura et al., "Chromosomal Manipulation by Site-Specific Recombinases and Fluorescent Protein-Based Vectors", PLOS One, vol. 5, No. 3, Mar. 24, 2010 (Mar. 24, 2010), p. E9846. XP055033795.
Metzger et al., Conditional Site-Specific Recombination in Mammaliancells Using a Ligand-Dependent Chimeric CRE Recombinase, Proceedings of the National Academy of Sciences. National Academy of Sciences, US, vol. 92, No. 15, Jul. 18, 1995 (Jul. 18, 1995), pp. 6991-6995, XP000615550.
Fu et al., "Split marker transformation increases homologous integration frequency in Cryptococcus neoformans", Fungal Genetics and Biology. San Diego, CA, US, vol. 43, No. 3, Mar. 1, 2006 (Mar. 1, 2006), pp. 200-212. XP024918894.
Bode et al., "The transgeneticist's toolbox: Novel methods for the targeted modification of eukaryotic genomes", Biological Chemistry. Walter De Gruyter GMBH & Co. Berlin, DE, vol. 381, No. 9-10, Sep. 1, 2000 (Sep. 1, 2000), pp. 801-813. XP002282829.

* cited by examiner

SEQUENCE LISTING

<160> NUMBER OF SEQ ID NOS: 31

<210> SEQ ID NO 1
<211> LENGTH: 1211
<212> TYPE: DNA
<213> ORGANISM: Artificial Sequence
<220> FEATURE:
<223> OTHER INFORMATION: 5' Cre recombinase synthetic fragment (Cre-1)

<400> SEQUENCE: 1

| | |
|---|---|
| ggcgcgccgc ggccgcaggc ctggcgccca gctggggccc gtcgacctcg agtaccgttc | 60 |
| gtataatgta tgctatacga agttatattt aaatctagta cggattagaa gccgccgagc | 120 |
| gggtgacagc cctccgaagg aagactctcc tccgtgcgtc ctcgtcttca ccggtcgcgt | 180 |
| tcctgaaacg cagatgtgcc tcgcgccgca ctgctccgaa caataaagat tctacaatac | 240 |
| tagcttttat ggttatgaag aggaaaaatt ggcagtaacc tggccccaca aaccttcaaa | 300 |
| tgaacgaatc aaattaacaa ccataggatg ataatgcgat tagttttta gccttatttc | 360 |
| tggggtaatt aatcagcgaa gcgatgattt ttgatctatt aacagatata taaatgcaaa | 420 |
| aactgcataa ccactttaac taatactttc aacattttcg gtttgtatta cttcttattc | 480 |
| aaatgtaata aaagtatcaa caaaaaattg ttaatatacc tctatacttt aacgtcaagg | 540 |
| agaaaaaacc ccggattcta gaactagtgg atccccggg ctgcaggaat tcgatatcaa | 600 |
| gcttatcgat accgtcgagg ggcagagccg atcctgtaca ctttacttaa aaccattatc | 660 |
| tgagtgttaa atgtccaatt tactgaccgt acaccaaaat ttgcctgcat taccggtcga | 720 |
| tgcaacgagt gatgaggttc gcaagaacct gatggacatg ttcagggatc gccaggcgtt | 780 |
| ttctgagcat acctggaaaa tgcttctgtc cgtttgccgg tcgtgggcgg catggtgcaa | 840 |
| gttgaataac cggaaatggt ttcccgcaga acctgaagat gttcgcgatt atcttctata | 900 |
| tcttcaggcg cgcggtctgg cagtaaaaac tatccagcaa catttgggcc agctaaacat | 960 |
| gcttcatcgt cggtccgggc tgccacgacc aagtgacagc aatgctgttt cactggttat | 1020 |
| gcggcggatc cgaaaagaaa acgttgatgc cggtgaacgt gcaaaacagg ctctagcgtt | 1080 |
| cgaacgcact gatttcgacc aggttcgttc actcatggaa aatagcgatc gctgccagga | 1140 |
| tatacgtaat ctggcatttc tggggattgc ttataacacc ctgttacgta tagccgaaat | 1200 |
| tgcggcgcgc c | 1211 |

<210> SEQ ID NO 2
<211> LENGTH: 1284
<212> TYPE: DNA
<213> ORGANISM: Artificial Sequence
<220> FEATURE:
<223> OTHER INFORMATION: 3' Cre recombinase synthetic fragment (Cre-2)

<400> SEQUENCE: 2

| | |
|---|---|
| ggccggcctt cgttcactca tggaaaatag cgatcgctgc aggatatac gtaatctggc | 60 |
| atttctgggg attgcttata acaccctgtt acgtatagcc gaaattgcca ggatcagggt | 120 |
| taaagatatc tcacgtactg acggtgggag aatgttaatc catattggca gaacgaaaac | 180 |
| gctggttagc accgcaggtg tagagaaggc acttagcctg gggtaacta aactggtcga | 240 |
| gcgatggatt tccgtctctg gtgtagctga tgatccgaat aactacctgt tttgccgggt | 300 |
| cagaaaaaat ggtgttgccg cgccatctgc caccagccag ctatcaactc gcgccctgga | 360 |
| agggattttt gaagcaactc atcgattgat ttacggcgct aaggatgact ctggtcagag | 420 |
| atacctggcc tggtctggac acagtgcccg tgtcggagcc gcgcgagata tggcccgcgc | 480 |

| | |
|---|---|
| tggagtttca ataccggaga tcatgcaagc tggtggctgg accaatgtaa atattgtcat | 540 |
| gaactatatc cgtaccctgg atagtgaaac aggggcaatg gtgcgcctgc tggaagatgg | 600 |
| cgattagcca ttaacgcgta aatgattgct ataattattt gatatttatg gtgacatatg | 660 |
| agaaaggatt tcaacatcga cggaaaatat gtagtgctgt ctgtaagcac taatattcag | 720 |
| tcgccagccg tcattgtcac tgtaaagctg agcgatagaa tgcctgatat tgactcaata | 780 |
| tccgttgcgt ttcctgtcaa agtatgcgt agtgctgaac atttcgtgat gaatgccacc | 840 |
| gaggaagaag cacggcgcgg ttttgcttaa agtgatgtct gagtttggcg aactcttggg | 900 |
| taaggttgga attgtcgacc tcgagtcatg taattagtta tgtcacgctt acattcacgc | 960 |
| cctcccccca catccgctct aaccgaaaag gaaggagtta gacaacctga agtctaggtc | 1020 |
| cctatttatt ttttatagt tatgttagta ttaagaacgt tatttatatt tcaaattttt | 1080 |
| cttttttttc tgtacagacg cgtgtacgca tgtaacatta tactgaaaac cttgcttgag | 1140 |
| aaggttttgg gacgctcgaa ggctttaatt tgcggccggt acataacttc gtataatgta | 1200 |
| tgctatacga acggtaggat ccgaattcgg gccccagctg ggcgccattt aaataggcct | 1260 |
| ggcgcgccgc ggccgcggcc ggcc | 1284 |

<210> SEQ ID NO 3
<211> LENGTH: 3581
<212> TYPE: DNA
<213> ORGANISM: Artificial Sequence
<220> FEATURE:
<223> OTHER INFORMATION: Complete sequence of pMA Cre1

<400> SEQUENCE: 3

| | |
|---|---|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg gtaacgccaa gggttttccc agtcacgacg ttgtaaaacg | 300 |
| acggccagtg agcgcgacgt aatacgactc actatagggc gaattggcgg aaggccgtca | 360 |
| aggcctaggc gcgccatgag ctcggcgcgc cgcggccgca ggcctggcgc ccagctgggg | 420 |
| cccgtcgacc tcgagtaccg ttcgtataat gtatgctata cgaagttata tttaaatcta | 480 |
| gtacggatta gaagccgccg agcgggtgac agccctccga aggaagactc tcctccgtgc | 540 |
| gtcctcgtct tcaccggtcg cgttcctgaa acgcagatgt gcctcgcgcc gcactgctcc | 600 |
| gaacaataaa gattctacaa tactagcttt tatggttatg aagaggaaaa attggcagta | 660 |
| acctggcccc acaaaccttc aaatgaacga atcaaattaa caaccatagg atgataatgc | 720 |
| gattagtttt ttagccttat ttctggggta attaatcagc gaagcgatga ttttttgatct | 780 |
| attaacagat atataaatgc aaaaactgca taaccacttt aactaatact ttcaacattt | 840 |
| tcggtttgta ttacttctta ttcaaatgta ataaaagtat caacaaaaaa ttgttaatat | 900 |
| acctctatac tttaacgtca aggagaaaaa accccggatt ctagaactag tggatccccc | 960 |
| gggctgcagg aattcgatat caagcttatc gataccgtcg aggggcagag ccgatcctgt | 1020 |
| acactttact aaaaccatt atctgagtgt taaatgtcca atttactgac cgtacaccaa | 1080 |
| aatttgcctg cattaccggt cgatgcaacg agtgatgagg ttcgcaagaa cctgatggac | 1140 |
| atgttcaggg atcgccaggc gttttctgag catacctgga aaatgcttct gtccgtttgc | 1200 |

```
cggtcgtggg cggcatggtg caagttgaat aaccggaaat ggtttcccgc agaacctgaa    1260
gatgttcgcg attatcttct atatcttcag gcgcgcggtc tggcagtaaa aactatccag    1320
caacatttgg gccagctaaa catgcttcat cgtcggtccg ggctgccacg accaagtgac    1380
agcaatgctg tttcactggt tatgcggcgg atccgaaaag aaaacgttga tgccggtgaa    1440
cgtgcaaaac aggctctagc gttcgaacgc actgatttcg accaggttcg ttcactcatg    1500
gaaaatagcg atcgctgcca ggatatacgt aatctggcat ttctggggat tgcttataac    1560
accctgttac gtatagccga aattgcggcg cgccggtacc tcttaattaa ctggcctcat    1620
gggccttccg ctcactgccc gctttccagt cgggaaacct gtcgtgccag ctgcattaac    1680
atggtcatag ctgtttcctt gcgtattggg cgctctccgc ttcctcgctc actgactcgc    1740
tgcgctcggt cgttcgggta agcctgggg tgcctaatga gcaaaaggcc agcaaaaggc     1800
caggaaccgt aaaaaggccg cgttgctggc gttttttccat aggctccgcc ccctgacga    1860
gcatcacaaa aatcgacgct caagtcagag gtggcgaaac ccgacaggac tataaagata    1920
ccaggcgttt ccccctggaa gctccctcgt gcgctctcct gttccgaccc tgccgcttac    1980
cggatacctg tccgcctttc tcccttcggg aagcgtggcg ctttctcata gctcacgctg    2040
taggtatctc agttcggtgt aggtcgttcg ctccaagctg ggctgtgtgc acgaaccccc    2100
cgttcagccc gaccgctgcg ccttatccgg taactatcgt cttgagtcca acccggtaag    2160
acacgactta tcgccactgg cagcagccac tggtaacagg attagcagag cgaggtatgt    2220
aggcggtgct acagagttct tgaagtggtg gcctaactac ggctacacta agaacagt      2280
atttggtatc tgcgctctgc tgaagccagt taccttcgga aaagagttg gtagctcttg     2340
atccggcaaa caaccaccg ctggtagcgg tggttttttt gtttgcaagc agcagattac     2400
gcgcagaaaa aaggatctc aagaagatcc tttgatcttt tctacggggt ctgacgctca     2460
gtggaacgaa aactcacgtt aagggatttt ggtcatgaga ttatcaaaaa ggatcttcac    2520
ctagatcctt ttaaattaaa aatgaagttt taaatcaatc taaagtatat atgagtaaac    2580
ttggtctgac agttaccaat gcttaatcag tgaggcacct atctcagcga tctgtctatt    2640
tcgttcatcc atagttgcct gactccccgt cgtgtagata actacgatac gggagggctt    2700
accatctggc cccagtgctg caatgatacc gcgagaacca cgctcaccgg ctccagattt    2760
atcagcaata aaccagccag ccggaagggc cgagcgcaga agtggtcctg caactttatc    2820
cgcctccatc cagtctatta ttgttgccgg gaagctaga gtaagtagtt cgccagttaa     2880
tagtttcgcc aacgttgttg ccattgctac aggcatcgtg gtgtcacgct cgtcgtttgg    2940
tatggcttca ttcagctccg gttcccaacg atcaaggcga gttacatgat cccccatgtt    3000
gtgcaaaaaa gcggttagct ccttcggtcc tccgatcgtt gtcagaagta agttggccgc    3060
agtgttatca ctcatggtta tggcagcact gcataattct cttactgtca tgccatccgt    3120
aagatgcttt tctgtgactg gtgagtactc aaccaagtca ttctgagaat agtgtatgcg    3180
gcgaccgagt tgctcttgcc cggcgtcaat acgggataat accgcgccac atagcagaac    3240
tttaaaagtg ctcatcattg gaaaacgttc ttcggggcga aaactctcaa ggatcttacc    3300
gctgttgaga tccagttcga tgtaacccac tcgtgcaccc aactgatctt cagcatcttt    3360
tactttcacc agcgtttctg ggtgagcaaa acaggaagg caaaatgccg caaaaaggg      3420
aataagggcg acacggaaat gttgaatact catactcttc cttttcaat attattgaag     3480
catttatcag ggttattgtc tcatgagcgg atacatattt gaatgtattt agaaaaataa    3540
acaaataggg gttccgcgca catttccccg aaaagtgcca c                        3581
```

<210> SEQ ID NO 4
<211> LENGTH: 3654
<212> TYPE: DNA
<213> ORGANISM: Artificial Sequence
<220> FEATURE:
<223> OTHER INFORMATION: Complete sequence of pMA Cre2 (pSUC225)

<400> SEQUENCE: 4

```
ctaaattgta agcgttaata ttttgttaaa attcgcgtta aatttttgtt aaatcagctc      60
attttttaac caataggccg aaatcggcaa atcccttat  aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgccatgag ctcggccggc cttcgttcac tcatggaaaa tagcgatcgc    420
tgccaggata tacgtaatct ggcatttctg gggattgctt ataacaccct gttacgtata    480
gccgaaattg ccaggatcag ggttaaagat atctcacgta ctgacggtgg agaatgtta    540
atccatattg gcagaacgaa aacgctggtt agcaccgcag gtgtagagaa ggcacttagc    600
ctggggggtaa ctaaactggt cgagcgatgg atttccgtct ctggtgtagc tgatgatccg    660
aataactacc tgttttgccg ggtcagaaaa atggtgttg ccgcgccatc tgccaccagc    720
cagctatcaa ctcgcgccct ggaagggatt tttgaagcaa ctcatcgatt gatttacggc    780
gctaaggatg actctggtca gagatacctg gcctggtctg gacacagtgc ccgtgtcgga    840
gccgcgcgag atatgcccg  cgctggagtt tcaataccgg agatcatgca agctggtggc    900
tggaccaatg taaatattgt catgaactat atccgtaccc tggatagtga aacagggca    960
atggtgcgcc tgctggaaga tggcgattag ccattaacgc gtaaatgatt gctataatta   1020
tttgatattt atggtgacat atgagaaagg atttcaacat cgacggaaaa tatgtagtgc   1080
tgtctgtaag cactaatatt cagtcgccag ccgtcattgt cactgtaaag ctgagcgata   1140
gaatgcctga tattgactca atatccgttg cgtttcctgt caaaagtatg cgtagtgctg   1200
aacatttcgt gatgaatgcc accgaggaag aagcacggcg cggttttgct taaagtgatg   1260
tctgagtttg gcgaactctt gggtaaggtt ggaattgtcg acctcgagtc atgtaattag   1320
ttatgtcacg cttacattca cgccctcccc ccacatccgc tctaaccgaa aggaaggag   1380
ttagacaacc tgaagtctag gtcccctattt attttttat  agttatgtta gtattaagaa   1440
cgttatttat atttcaaatt tttcttttt  ttctgtacag acgcgtgtac gcatgtaaca   1500
ttatactgaa aaccttgctt gagaaggttt tgggacgctc gaaggcttta atttgcggcc   1560
ggtacataac ttcgtataat gtatgctata cgaacggtag gatccgaatt cgggccccag   1620
ctgggcgcca tttaaatagg cctggcgcgc gcggccgcg  gccggccggt acctcttaat   1680
taactggcct catgggcctt ccgctcactg cccgctttcc agtcgggaaa cctgtcgtgc   1740
cagctgcatt aacatggtca tagctgtttc cttgcgtatt gggcgctctc cgcttcctcg   1800
ctcactgact cgctgcgctc ggtcgttcgg gtaaagcctg gggtgcctaa tgagcaaaag   1860
gccagcaaaa ggccaggaac cgtaaaaagg ccgcgttgct ggcgtttttc cataggctcc   1920
gcccccctga cgagcatcac aaaaatcgac gctcaagtca gaggtggcga aacccgacag   1980
gactataaag ataccaggcg tttccccctg gaagctccct cgtgcgctct cctgttccga   2040
```

```
ccctgccgct taccggatac ctgtccgcct ttctcccttc gggaagcgtg gcgctttctc    2100
atagctcacg ctgtaggtat ctcagttcgg tgtaggtcgt tcgctccaag ctgggctgtg    2160
tgcacgaacc ccccgttcag cccgaccgct gcgccttatc cggtaactat cgtcttgagt    2220
ccaacccggt aagacacgac ttatcgccac tggcagcagc cactggtaac aggattagca    2280
gagcgaggta tgtaggcggt gctacagagt tcttgaagtg gtggcctaac tacggctaca    2340
ctagaagaac agtatttggt atctgcgctc tgctgaagcc agttaccttc ggaaaaagag    2400
ttggtagctc ttgatccggc aaacaaacca ccgctggtag cggtggtttt tttgtttgca    2460
agcagcagat tacgcgcaga aaaaaaggat ctcaagaaga tcctttgatc ttttctacgg    2520
ggtctgacgc tcagtggaac gaaaactcac gttaagggat tttggtcatg agattatcaa    2580
aaaggatctt cacctagatc cttttaaatt aaaaatgaag ttttaaatca atctaaagta    2640
tatatgagta aacttggtct gacagttacc aatgcttaat cagtgaggca cctatctcag    2700
cgatctgtct atttcgttca tccatagttg cctgactccc cgtcgtgtag ataactacga    2760
tacgggaggg cttaccatct ggccccagtg ctgcaatgat accgcgagaa ccacgctcac    2820
cggctccaga tttatcagca ataaaccagc cagccggaag ggccgagcgc agaagtggtc    2880
ctgcaacttt atccgcctcc atccagtcta ttaattgttg ccgggaagct agagtaagta    2940
gttcgccagt taatagtttg cgcaacgttg ttgccattgc tacaggcatc gtggtgtcac    3000
gctcgtcgtt tggtatggct tcattcagct ccggttccca acgatcaagg cgagttacat    3060
gatcccccat gttgtgcaaa aaagcggtta gctccttcgg tcctccgatc gttgtcagaa    3120
gtaagttggc cgcagtgtta tcactcatgg ttatggcagc actgcataat tctcttactg    3180
tcatgccatc cgtaagatgc ttttctgtga ctggtgagta ctcaaccaag tcattctgag    3240
aatagtgtat gcggcgaccg agttgctctt gcccggcgtc aatacgggat aataccgcgc    3300
cacatagcag aactttaaaa gtgctcatca ttggaaaacg ttcttcgggg cgaaaactct    3360
caaggatctt accgctgttg agatccagtt cgatgtaacc cactcgtgca cccaactgat    3420
cttcagcatc ttttactttc accagcgttt ctgggtgagc aaaaacagga aggcaaaatg    3480
ccgcaaaaaa gggaataagg gcgacacgga aatgttgaat actcatactc ttcctttttc    3540
aatattattg aagcatttat cagggttatt gtctcatgag cggatacata tttgaatgta    3600
tttagaaaaa taaacaaata ggggttccgc gcacatttcc ccgaaaagtg ccac          3654
```

<210> SEQ ID NO 5
<211> LENGTH: 3982
<212> TYPE: DNA
<213> ORGANISM: Artificial Sequence
<220> FEATURE:
<223> OTHER INFORMATION: Complete sequence of pUG7-EcoRV

<400> SEQUENCE: 5

```
gaacgcggcc gccagctgaa gcttcgtacg ctgcaggtcg acgaattcta ccgttcgtat      60
aatgtatgct atacgaagtt atagatctgt ttagcttgcc tcgtcccgc cgggtcaccc     120
ggccagcgac atggaggccc agaataccct ccttgacagt cttgacgtgc gcagctcagg    180
ggcatgatgt gactgtcgcc cgtacattta gcccatacat ccccatgtat aatcatttgc    240
atccatacat tttgatggcc gcacggcgcg aagcaaaaat tacggctcct cgctgcagac    300
ctgcgagcag ggaaacgctc ccctcacaga cgcgttgaat tgtccccacg ccgcgcccct    360
gtagagaaat ataaaaggtt aggatttgcc actgaggttc ttctttcata tacttccttt    420
taaaatcttg ctaggataca gttctcacat cacatccgaa cataaacaac catgggtaag    480
```

```
gaaaagactc acgtttcgag gccgcgatta aattccaaca tggatgctga tttatatggg      540
tataaatggg ctcgcgataa tgtcgggcaa tcaggtgcga caatctatcg attgtatggg      600
aagcccgatg cgccagagtt gtttctgaaa catggcaaag gtagcgttgc caatgatgtt      660
acagatgaga tggtcagact aaactggctg acggaattta tgcctcttcc gaccatcaag      720
cattttatcc gtactcctga tgatgcatgg ttactcacca ctgcgatccc cggcaaaaca      780
gcattccagg tattagaaga atatcctgat tcaggtgaaa atattgttga tgcgctggca      840
gtgttcctgc gccggttgca ttcgattcct gtttgtaatt gtccttttaa cagcgatcgc      900
gtatttcgtc tcgctcaggc gcaatcacga atgaataacg gtttggttga tgcgagtgat      960
tttgatgacg agcgtaatgg ctggcctgtt gaacaagtct ggaaagaaat gcataagctt     1020
ttgccattct caccggattc agtcgtcact catggtgatt tctcacttga taaccttatt     1080
tttgacgagg ggaaattaat aggttgtatt gatgttggac gagtcggaat cgcagaccga     1140
taccaggatc ttgccatcct atggaactgc ctcggtgagt tttctccttc attacagaaa     1200
cggcttttc aaaaatatgg tattgataat cctgatatga ataaattgca gtttcatttg     1260
atgctcgatg agttttcta atcagtactg acaataaaaa gattcttgtt ttcaagaact     1320
tgtcatttgt atagttttt tatattgtag ttgttctatt ttaatcaaat gttagcgtga     1380
tttatatttt ttttcgcctc gacatcatct gcccagatgc gaagttaagt gcgcagaaag     1440
taatatcatg cgtcaatcgt atgtgaatgc tggtcgctat actgctgtcg attcgatact     1500
aacgccgcca tccagtgtcg aaaacgagct cataacttcg tataatgtat gctatacgaa     1560
cggtagaatt cgatatcaga tccactagtg gcctatgcgg ccgcggatct gccggtctcc     1620
ctatagtgag tcgtattaat ttcgataagc caggttaacc tgcattaatg aatcggccaa     1680
cgcgcgggga gaggcggttt gcgtattggg cgctcttccg cttcctcgct cactgactcg     1740
ctgcgctcgg tcgttcggct gcggcgagcg gtatcagctc actcaaaggc ggtaatacgg     1800
ttatccacag aatcagggga taacgcagga agaacatgt gagcaaaagg ccagcaaaag     1860
gccaggaacc gtaaaaaggc cgcgttgctg gcgtttttcc ataggctccg ccccctgac     1920
gagcatcaca aaaatcgacg ctcaagtcag aggtggcgaa acccgacagg actataaaga     1980
taccaggcgt ttccccctgg aagctccctc gtgcgctctc ctgttccgac cctgccgctt     2040
accggatacc tgtccgcctt tctcccttcg ggaagcgtgg cgctttctca atgctcacgc     2100
tgtaggtatc tcagttcggt gtaggtcgtt cgctccaagc tgggctgtgt gcacgaaccc     2160
cccgttcagc ccgaccgctg cgccttatcc ggtaactatc gtcttgagtc aacccggta     2220
agacacgact tatcgccact ggcagcagcc actggtaaca ggattagcag agcgaggtat     2280
gtaggcggtg ctacagagtt cttgaagtgg tggcctaact acggctacac tagaaggaca     2340
gtatttggta tctgcgctct gctgaagcca gttaccttcg aaaaagagt tggtagctct     2400
tgatccggca aacaaccac cgctggtagc ggtggtttt ttgtttgcaa gcagcagatt     2460
acgcgcagaa aaaaaggatc tcaagaagat cctttgatct tttctacggg gtctgacgct     2520
cagtggaacg aaaactcacg ttaagggatt ttggtcatga gattatcaaa aaggatcttc     2580
acctagatcc ttttaaatta aaatgaagt tttaaatcaa tctaaagtat atatgagtaa     2640
acttggtctg acagttacca atgcttaatc agtgaggcac ctatctcagc gatctgtcta     2700
tttcgttcat ccatagttgc ctgactcccc gtcgtgtaga taactacgat acgggagggc     2760
ttaccatctg gccccagtgc tgcaatgata ccgcgagacc cacgctcacc ggctccagat     2820
```

| | | |
|---|---|---|
| ttatcagcaa taaaccagcc agccggaagg gccgagcgca gaagtggtcc tgcaacttta | | 2880 |
| tccgcctcca tccagtctat taattgttgc cgggaagcta gagtaagtag ttcgccagtt | | 2940 |
| aatagtttgc gcaacgttgt tgccattgct acaggcatcg tggtgtcacg ctcgtcgttt | | 3000 |
| ggtatggctt cattcagctc cggttcccaa cgatcaaggc gagttacatg atcccccatg | | 3060 |
| ttgtgcaaaa aagcggttag ctccttcggt cctccgatcg ttgtcagaag taagttggcc | | 3120 |
| gcagtgttat cactcatggt tatggcagca ctgcataatt ctcttactgt catgccatcc | | 3180 |
| gtaagatgct tttctgtgac tggtgagtac tcaaccaagt cattctgaga atagtgtatg | | 3240 |
| cggcgaccga gttgctcttg cccggcgtca atacgggata taccgcgcc acatagcaga | | 3300 |
| actttaaaag tgctcatcat tggaaaacgt tcttcgggg gaaaactctc aaggatctta | | 3360 |
| ccgctgttga gatccagttc gatgtaaccc actcgtgcac ccaactgatc ttcagcatct | | 3420 |
| tttactttca ccagcgtttc tgggtgagca aaaacaggaa ggcaaaatgc cgcaaaaaag | | 3480 |
| ggaataaggg cgacacggaa atgttgaata ctcatactct tccttttca atattattga | | 3540 |
| agcatttatc agggttattg tctcatgagc ggatacatat ttgaatgtat ttagaaaaat | | 3600 |
| aaacaaatag gggttccgcg cacatttccc cgaaaagtgc cacctgacgt ctaagaaacc | | 3660 |
| attattatca tgacattaac ctataaaaat aggcgtatca cgaggccctt tcgtctcgcg | | 3720 |
| cgtttcggtg atgacggtga aaacctctga cacatgcagc tcccggagac ggtcacagct | | 3780 |
| tgtctgtaag cggatgccgg gagcagacaa gcccgtcagg gcgcgtcagc gggtgttggc | | 3840 |
| gggtgtcggg gctggcttaa ctatgcggca tcagagcaga ttgtactgag agtgcaccat | | 3900 |
| atggacatat tgtcgttaga acgcggctac aattaataca taaccttatg tatcatacac | | 3960 |
| atacgattta ggtgacacta ta | | 3982 |

<210> SEQ ID NO 6
<211> LENGTH: 32
<212> TYPE: DNA
<213> ORGANISM: Artificial Sequence
<220> FEATURE:
<223> OTHER INFORMATION: Primer DBC-02738

<400> SEQUENCE: 6
aaggatttaa atgacatgga ggcccagaat ac                                 32

<210> SEQ ID NO 7
<211> LENGTH: 32
<212> TYPE: DNA
<213> ORGANISM: Artificial Sequence
<220> FEATURE:
<223> OTHER INFORMATION: Primer DBC-02739

<400> SEQUENCE: 7
aaggatttaa atcagtatag cgaccagcat tc                                 32

<210> SEQ ID NO 8
<211> LENGTH: 4900
<212> TYPE: DNA
<213> ORGANISM: Artificial Sequence
<220> FEATURE:
<223> OTHER INFORMATION: pCR-Blunt II-TOPO vector with kanMX marker PCR fragment

<400> SEQUENCE: 8
agcgcccaat acgcaaaccg cctctccccg cgcgttggcc gattcattaa tgcagctggc        60
acgacaggtt tcccgactgg aaagcgggca gtgagcgcaa cgcaattaat gtgagttagc       120

-continued

| | |
|---|---|
| tcactcatta ggcacccag gctttacact ttatgcttcc ggctcgtatg ttgtgtggaa | 180 |
| ttgtgagcgg ataacaattt cacacaggaa acagctatga ccatgattac gccaagctat | 240 |
| ttaggtgaca ctatagaata ctcaagctat gcatcaagct tggtaccgag ctcggatcca | 300 |
| ctagtaacgg ccgccagtgt gctggaattc gcccttaagg atttaaatga catggaggcc | 360 |
| cagaataccc tccttgacag tcttgacgtg cgcagctcag gggcatgatg tgactgtcgc | 420 |
| ccgtacattt agcccataca tccccatgta taatcatttg catccataca ttttgatggc | 480 |
| cgcacggcgc gaagcaaaaa ttacggctcc tcgctgcaga cctgcgagca gggaaacgct | 540 |
| cccctcacag acgcgttgaa ttgtccccac gccgcgcccc tgtagagaaa tataaaaggt | 600 |
| taggatttgc cactgaggtt cttctttcat atacttcctt ttaaaatctt gctaggatac | 660 |
| agttctcaca tcatccga acataaacaa ccatgggtaa ggaaaagact cacgtttcga | 720 |
| ggccgcgatt aaattccaac atggatgctg atttatatgg gtataaatgg gctcgcgata | 780 |
| atgtcgggca atcaggtgcg acaatctatc gattgtatgg gaagcccgat gcgccagagt | 840 |
| tgtttctgaa acatggcaaa ggtagcgttg ccaatgatgt tacagatgag atggtcagac | 900 |
| taaactggct gacggaattt atgcctcttc cgaccatcaa gcattttatc cgtactcctg | 960 |
| atgatgcatg gttactcacc actgcgatcc ccggcaaaac agcattccag gtattagaag | 1020 |
| aatatcctga ttcaggtgaa atattgttg atgcgctggc agtgttcctg cgccggttgc | 1080 |
| attcgattcc tgtttgtaat tgtccttta acagcgatcg cgtatttcgt ctcgctcagg | 1140 |
| cgcaatcacg aatgaataac ggtttggttg atgcgagtga ttttgatgac gagcgtaatg | 1200 |
| gctggcctgt tgaacaagtc tggaaagaaa tgcataagct tttgccattc tcaccggatt | 1260 |
| cagtcgtcac tcatggtgat ttctcacttg ataaccttat ttttgacgag gggaaattaa | 1320 |
| taggttgtat tgatgttgga cgagtcggaa tcgcagaccg ataccaggat cttgccatcc | 1380 |
| tatggaactg cctcggtgag ttttctcctt cattacagaa acggcttttt caaaaatatg | 1440 |
| gtattgataa tcctgatatg aataaattgc agtttcattt gatgctcgat gagttttct | 1500 |
| aatcagtact gacaataaaa agattcttgt tttcaagaac ttgtcatttg tatagttttt | 1560 |
| ttatattgta gttgttctat tttaatcaaa tgttagcgtg atttatattt tttttcgcct | 1620 |
| cgacatcatc tgcccagatg cgaagttaag tgcgcagaaa gtaatatcat gcgtcaatcg | 1680 |
| tatgtgaatg ctggtcgcta tactgattta aatccttaag gcgaattct gcagatatcc | 1740 |
| atcacactgg cggccgctcg agcatgcatc tagagggccc aattcgccct atagtgagtc | 1800 |
| gtattacaat tcactggccg tcgttttaca acgtcgtgac tgggaaaacc ctggcgttac | 1860 |
| ccaacttaat cgccttgcag cacatccccc tttcgccagc tggcgtaata gcgaagaggc | 1920 |
| ccgcaccgat cgcccttccc aacagttgcg cagcctatac gtacggcagt ttaaggttta | 1980 |
| cacctataaa agagagagcc gttatcgtct gtttgtggat gtacagagtg atattattga | 2040 |
| cacgccgggg cgacggatgg tgatcccct ggccagtgca cgtctgctgt cagataaagt | 2100 |
| ctcccgtgaa ctttacccgg tggtgcatat cggggatgaa agctggcgca tgatgaccac | 2160 |
| cgatatggcc agtgtgccgg tctccgttat cggggaagaa gtggctgatc tcagccaccg | 2220 |
| cgaaaatgac atcaaaaacg ccattaacct gatgttctgg ggaatataaa tgtcaggcat | 2280 |
| gagattatca aaaaggatct tcacctagat ccttttcacg tagaaagcca gtccgcagaa | 2340 |
| acggtgctga ccccggatga atgtcagcta ctgggctatc tggacaaggg aaaacgcaag | 2400 |
| cgcaaagaga agcaggtag cttgcagtgg gcttacatgg cgatagctag actgggcggt | 2460 |
| tttatggaca gcaagcgaac cggaattgcc agctggggcg ccctctggta aggttgggaa | 2520 |

```
gccctgcaaa gtaaactgga tggctttctc gccgccaagg atctgatggc gcagggatc     2580 aagctctgat caagagacag gatgaggatc gtttcgcatg attgaacaag atggattgca    2640
cgcaggttct ccggccgctt gggtggagag gctattcggc tatgactggg cacaacagac    2700
aatcggctgc tctgatgccg ccgtgttccg gctgtcagcg caggggcgcc cggttctttt    2760
tgtcaagacc gacctgtccg gtgccctgaa tgaactgcaa gacgaggcag cgcggctatc    2820
gtggctggcc acgacgggcg ttccttgcgc agctgtgctc gacgttgtca ctgaagcggg    2880
aagggactgg ctgctattgg gcgaagtgcc ggggcaggat ctcctgtcat ctcaccttgc    2940
tcctgccgag aaagtatcca tcatggctga tgcaatgcgg cggctgcata cgcttgatcc    3000
ggctacctgc ccattcgacc accaagcgaa acatcgcatc gagcgagcac gtactcggat    3060
ggaagccggt cttgtcgatc aggatgatct ggacgaagag catcaggggc tcgcgccagc    3120
cgaactgttc gccaggctca aggcgagcat gcccgacggc gaggatctcg tcgtgaccca    3180
tggcgatgcc tgcttgccga atatcatggt ggaaaatggc cgcttttctg gattcatcga    3240
ctgtggccgg ctgggtgtgg cggaccgcta tcaggacata gcgttggcta cccgtgatat    3300
tgctgaagag cttggcggcg aatgggctga ccgcttcctc gtgctttacg gtatcgccgc    3360
tcccgattcg cagcgcatcg ccttctatcg ccttcttgac gagttcttct gaattattaa    3420
cgcttacaat ttcctgatgc ggtattttct ccttacgcat ctgtgcggta tttcacaccg    3480
catacaggtg gcacttttcg gggaaatgtg cgcggaaccc ctatttgttt attttctaa    3540 atacattcaa atatgtatcc gctcatgaga caataaccct gataaatgct tcaataatag    3600
cacgtgagga gggccaccat ggccaagttg accagtgccg ttccggtgct caccgcgcgc    3660
gacgtcgccg gagcggtcga gttctggacc gaccggctcg ggttctcccg gacttcgtg    3720 gaggacgact tcgccggtgt ggtccgggac gacgtgaccc tgttcatcag cgcggtccag    3780
gaccaggtgg tgccggacaa caccctggcc tgggtgtggg tgcgcggcct ggacgagctg    3840
tacgccgagt ggtcggaggt cgtgtccacg aacttccggg acgcctccgg ccggccatg    3900 accgagatcg gcgagcagcc gtgggggcgg gagttcgccc tgcgcgaccc ggccggcaac    3960
tgcgtgcact tcgtggccga ggagcaggac tgacacgtgc taaaacttca tttttaattt    4020
aaaaggatct aggtgaagat cctttttgat aatctcatga ccaaaatccc ttaacgtgag    4080
ttttcgttcc actgagcgtc agaccccgta gaaaagatca aaggatcttc ttgagatcct    4140 tttttctgc gcgtaatctg ctgcttgcaa acaaaaaaac caccgctacc agcggtggtt    4200
tgtttgccga atcaagagct accaactctt tttccgaagg taactggctt cagcagagcg    4260
cagataccaa atactgtcct tctagtgtag ccgtagttag gccaccactt caagaactct    4320
gtagcaccgc ctacatacct cgctctgcta atcctgttac cagtggctgc tgccagtggc    4380
gataagtcgt gtcttaccgg gttggactca agacgatagt taccggataa ggcgcagcgg    4440
tcgggctgaa cggggggttc gtgcacacag cccagcttgg agcgaacgac ctacaccgaa    4500
ctgagatacc tacagcgtga gctatgagaa agcgccacgc ttcccgaagg gagaaaggcg    4560
gacaggtatc cggtaagcgg cagggtcgga acaggagagc gcacgaggga gcttccaggg    4620
ggaaacgcct ggtatcttta tagtcctgtc gggtttcgcc acctctgact tgagcgtcga    4680
tttttgtgat gctcgtcagg ggggcggagc ctatggaaaa acgccagcaa cgcggccttt    4740
ttacggttcc tggccttttg ctggccttttt gctcacatgt tctttcctgc gttatcccct    4800
gattctgtgg ataaccgtat taccgccttt gagtgagctg ataccgctcg ccgcagccga    4860
```
acgaccgagc gcagcgagtc agtgagcgag gaagcggaag         4900

<210> SEQ ID NO 9
<211> LENGTH: 4946
<212> TYPE: DNA
<213> ORGANISM: Artificial Sequence
<220> FEATURE:
<223> OTHER INFORMATION: Full sequence of pSUC227

<400> SEQUENCE: 9
aaatctagta cggattagaa gccgccgagc gggtgacagc cctccgaagg aagactctcc    60
tccgtgcgtc ctcgtcttca ccggtcgcgt tcctgaaacg cagatgtgcc tcgcgccgca   120
ctgctccgaa caataaagat tctacaatac tagcttttat ggttatgaag aggaaaaatt   180
ggcagtaacc tggccccaca aaccttcaaa tgaacgaatc aaattaacaa ccataggatg   240
ataatgcgat tagttttttta gccttatttc tggggtaatt aatcagcgaa gcgatgattt   300
ttgatctatt aacagatata taatgcaaa aactgcataa ccactttaac taatactttc   360
aacattttcg gtttgtatta cttcttattc aaatgtaata aaagtatcaa caaaaaattg   420
ttaatatacc tctatacttt aacgtcaagg agaaaaaacc ccggattcta gaactagtgg   480
atccccgggg ctgcaggaat tcgatatcaa gcttatcgat accgtcgagg ggcagagccg   540
atcctgtaca ctttacttaa aaccattatc tgagtgttaa atgtccaatt tactgaccgt   600
acaccaaaat ttgcctgcat taccggtcga tgcaacgagt gatgaggttc gcaagaacct   660
gatggacatg ttcagggatc gccaggcgtt ttctgagcat acctggaaaa tgcttctgtc   720
cgtttgccgg tcgtgggcgg catggtgcaa gttgaataac cggaaatggt ttcccgcaga   780
acctgaagat gttcgcgatt atcttctata tcttcaggcg cgcggtctgg cagtaaaaac   840
tatccagcaa catttgggcc agctaaacat gcttcatcgt cggtccgggc tgccacgacc   900
aagtgacagc aatgctgttt cactggttat gcggcggatc cgaaaagaaa acgttgatgc   960
cggtgaacgt gcaaaacagg ctctagcgtt cgaacgcact gatttcgacc aggttcgttc  1020
actcatggaa aatagcgatc gctgccagga tacgtaat ctggcatttc tggggattgc  1080
ttataacacc ctgttacgta tagccgaaat tgccgcgcgc cggtacctct taattaactg  1140
gcctcatggg ccttccgctc actgcccgct ttccagtcgg gaaacctgtc gtgccagctg  1200
cattaacatg gtcatagctg tttccttgcg tattgggcgc tctccgcttc ctcgctcact  1260
gactcgctgc gctcggtcgt tcgggtaaag cctggggtgc ctaatgagca aaaggccagc  1320
aaaaggccag gaaccgtaaa aaggccgcgt tgctggcgtt tttccatagg ctccgccccc  1380
ctgacgagca tcacaaaaat cgacgctcaa gtcagaggtg gcgaaacccg acaggactat  1440
aaagatacca ggcgtttccc cctggaagct ccctcgtgcg ctctcctgtt ccgaccctgc  1500
cgcttaccgg atacctgtcc gcctttctcc cttcgggaag cgtggcgctt tctcatagct  1560
cacgctgtag gtatctcagt tcggtgtagg tcgttcgctc caagctgggc tgtgtgcacg  1620
aaccccccgt tcagcccgac cgctgcgcct tatccggtaa ctatcgtctt gagtccaacc  1680
cggtaagaca cgacttatcg ccactggcag cagccactgg taacaggatt agcagagcga  1740
ggtatgtagg cggtgctaca gagttcttga agtggtggcc taactacggc tacactagaa  1800
gaacagtatt tggtatctgc gctctgctga agccagttac cttcggaaaa agagttggta  1860
gctcttgatc cggcaaacaa accaccgctg gtagcggtgg ttttttttgtt tgcaagcagc  1920
agattacgcg cagaaaaaaa ggatctcaag aagatccttt gatcttttct acggggtctg  1980
acgctcagtg gaacgaaaac tcacgttaag ggattttggt catgagatta tcaaaaagga  2040

```
tcttcaccta gatcctttta aattaaaaat gaagttttaa atcaatctaa agtatatatg    2100
agtaaacttg gtctgacagt taccaatgct taatcagtga ggcacctatc tcagcgatct    2160
gtctatttcg ttcatccata gttgcctgac tccccgtcgt gtagataact acgatacggg    2220
agggcttacc atctggcccc agtgctgcaa tgataccgcg agaaccacgc tcaccggctc    2280
cagatttatc agcaataaac cagccagccg gaagggccga gcgcagaagt ggtcctgcaa    2340
ctttatccgc ctccatccag tctattaatt gttgccggga agctagagta agtagttcgc    2400
cagttaatag tttgcgcaac gttgttgcca ttgctacagg catcgtggtg tcacgctcgt    2460
cgtttggtat ggcttcattc agctccggtt cccaacgatc aaggcgagtt acatgatccc    2520
ccatgttgtg caaaaaagcg gttagctcct tcggtcctcc gatcgttgtc agaagtaagt    2580
tggccgcagt gttatcactc atggttatgg cagcactgca taattctctt actgtcatgc    2640
catccgtaag atgcttttct gtgactggtg agtactcaac caagtcattc tgagaatagt    2700
gtatgcggcg accgagttgc tcttgcccgg cgtcaatacg ggataatacc gcgccacata    2760
gcagaacttt aaaagtgctc atcattggaa aacgttcttc ggggcgaaaa ctctcaagga    2820
tcttaccgct gttgagatcc agttcgatgt aacccactcg tgcacccaac tgatcttcag    2880
catcttttac tttcaccagc gtttctgggt gagcaaaaac aggaaggcaa aatgccgcaa    2940
aaaagggaat aagggcgaca cggaaatgtt gaatactcat actcttcctt tttcaatatt    3000
attgaagcat ttatcagggt tattgtctca tgagcggata catatttgaa tgtatttaga    3060
aaaataaaca aataggggtt ccgcgcacat ttccccgaaa agtgccacct aaattgtaag    3120
cgttaatatt ttgttaaaat tcgcgttaaa ttttttgttaa atcagctcat tttttaacca    3180
ataggccgaa atcggcaaaa tcccttataa atcaaaagaa tagaccgaga tagggttgag    3240
tggccgctac agggcgctcc cattcgccat tcaggctgcg caactgttgg gaagggcgtt    3300
tcggtgcggg cctcttcgct attacgccag ctggcgaaag ggggatgtgc tgcaaggcga    3360
ttaagttggg taacgccagg gttttcccag tcacgacgtt gtaaaacgac ggccagtgag    3420
cgcgacgtaa tacgactcac tatagggcga attggcggaa ggccgtcaag gcctaggcgc    3480
gccatgagct cggcgcgccg cggccgcagg cctggcgccc agctggggcc cgtcgacctc    3540
gagtaccgtt cgtataatgt atgctatacg aagttatatt taaatcagta tagcgaccag    3600
cattcacata cgattgacgc atgatattac tttctgcgca cttaacttcg catctgggca    3660
gatgatgtcg aggcgaaaaa aaatataaat cacgctaaca tttgattaaa atagaacaac    3720
tacaatataa aaaactata caaatgacaa gttcttgaaa acaagaatct ttttattgtc    3780
agtactgatt agaaaaactc atcgagcatc aaatgaaact gcaatttatt catatcagga    3840
ttatcaatac catattttg aaaaagccgt tctgtaatg aaggagaaaa ctcaccgagg    3900
cagttccata ggatggcaag atcctggtat cggtctgcga ttccgactcg tccaacatca    3960
atacaaccta ttaatttccc ctcgtcaaaa ataaggttat caagtgagaa atcaccatga    4020
gtgacgactg aatccggtga gaatggcaaa agcttatgca tttctttcca gacttgttca    4080
acaggccagc cattacgctc gtcatcaaaa tcactcgcat caaccaaacc gttattcatt    4140
cgtgattgcg cctgagcgag acgaaatacg cgatcgctgt taaaaggaca attacaaaca    4200
ggaatcgaat gcaaccggcg caggaacact gccagcgcat caacaatatt ttcacctgaa    4260
tcaggatatt cttctaatac ctggaatgct gttttgccgg ggatcgcagt ggtgagtaac    4320
catgcatcat caggagtacg gataaaatgc ttgatggtcg gaagaggcat aaattccgtc    4380
```

```
agccagttta gtctgaccat ctcatctgta acatcattgg caacgctacc tttgccatgt    4440
ttcagaaaca actctggcgc atcgggcttc ccatacaatc gatagattgt cgcacctgat    4500
tgcccgacat tatcgcgagc ccatttatac ccatataaat cagcatccat gttggaattt    4560
aatcgcggcc tcgaaacgtg agtcttttcc ttacccatgg ttgtttatgt tcggatgtga    4620
tgtgagaact gtatcctagc aagattttaa aaggaagtat atgaaagaag aacctcagtg    4680
gcaaatccta acctttttata tttctctaca ggggcgcggc gtggggacaa ttcaacgcgt    4740
ctgtgagggg agcgtttccc tgctcgcagg tctgcagcga ggagccgtaa tttttgcttc    4800
gcgccgtgcg gccatcaaaa tgtatggatg caaatgatta tacatgggga tgtatgggct    4860
aaatgtacgg gcgacagtca catcatgccc ctgagctgcg cacgtcaaga ctgtcaagga    4920
gggtattctg ggcctccatg tcattt                                        4946

<210> SEQ ID NO 10
<211> LENGTH: 629
<212> TYPE: DNA
<213> ORGANISM: Artificial Sequence
<220> FEATURE:
<223> OTHER INFORMATION: 5' flanking fragment upstream of the ICL1 gene

<400> SEQUENCE: 10
cgtagcatag ttgcgagcaa gggaaggcaa cacagttaaa atgacaatgt tagaaggaaa     60
aactaaatca agctcccata ggaaatttct tgtgtcagta atatgtctcg agaaaataat    120 ataattgaa tctatttatt gaaaagtaaa tatctcgtaa cccggatgct ttgggcggtc    180
gggttttgct actcgtcatc cgatgagaaa aactgttccc ttttgcccca ggtttccatt    240
catccgagcg atcacttatc tgacttcgtc acttttcat ttcatccgaa acaatcaaaa    300
ctgaagccaa tcaccacaaa attaacactc aacgtcatct ttcactaccc tttacagaag    360
aaaatatcca tagtccggac tagcatccca gtatgtgact caatattggt gcaaaagaga    420
aaagcataag tcagtccaaa gtccgccctt aaccaggcac atcggaattc acaaaacgtt    480
tctttattat ataaaggagc tgcttcactg gcaaaattct tattatttgt cttggcttgc    540
taatttcatc ttatcctttt tttctttca cacccaaata cctaacaatt gagagaaaac    600
tcttagcata acataacaaa aagtcaacg                                     629

<210> SEQ ID NO 11
<211> LENGTH: 28
<212> TYPE: DNA
<213> ORGANISM: Artificial Sequence
<220> FEATURE:
<223> OTHER INFORMATION: Primer sequence DBC-03754

<400> SEQUENCE: 11
cgtagcatag ttgcgagcaa gggaaggc                                       28

<210> SEQ ID NO 12
<211> LENGTH: 59
<212> TYPE: DNA
<213> ORGANISM: Artificial Sequence
<220> FEATURE:
<223> OTHER INFORMATION: Primer sequence DBC-03755

<400> SEQUENCE: 12
cgttgacttt tgttatgtt atgctaagag ttttctctca attgttaggt atttgggtg       59

<210> SEQ ID NO 13
<211> LENGTH: 603
```

```
<212> TYPE: DNA
<213> ORGANISM: Artificial Sequence
<220> FEATURE:
<223> OTHER INFORMATION: 3' flanking fragment downstream of the ICL1
      gene

<400> SEQUENCE: 13
gaaataggac aaggattaac cattagaact gccggcattt cctgacaagt atatatattc      60
gtaatctcaa tgtatatttt tttcatatat aaacatgcgt acttaaaaac ttaaactcat     120
cgttactgca gtacaatgtt ctctaatggc atctctctaa tggtactcca actaaagtca     180
acattctctc cgtgcaagaa tgcctttctc tagttgcaaa aacgagtcaa taaacatctt     240
tgatcgagtc gcctcatttt tgttgactcg gtgactaaaa tcagtgccat ttctgtccat     300
gcctcgtgcg cgaatgattg aatcgaacta atcccgaaca caatcatagt atcgtatcgc     360
ccattagtgc cgtgagtgta cgcgaggcaa aaggcaccat ggaaaatatt cccttagtca     420
tcttggaaat cattgagact gtaaaggaac tcgcaaacgg gtaaccgata tttaccccac     480
ctttggtcga gaaattccac ctgttcggca attttttgccg ctcttctcaa gagcaaaagg     540
cgttttttttt tctgacacgc ctcttctctc gcatgccaaa ctcaagcgtc ctacatgctt     600
ttc                                                                    603

<210> SEQ ID NO 14
<211> LENGTH: 33
<212> TYPE: DNA
<213> ORGANISM: Artificial Sequence
<220> FEATURE:
<223> OTHER INFORMATION: Primer sequence DBC-03758

<400> SEQUENCE: 14
gaaataggac aaggattaac cattagaact gcc                                   33

<210> SEQ ID NO 15
<211> LENGTH: 29
<212> TYPE: DNA
<213> ORGANISM: Artificial Sequence
<220> FEATURE:
<223> OTHER INFORMATION: Primer sequence DBC-03759

<400> SEQUENCE: 15
gaaaagcatg taggacgctt gagtttggc                                        29

<210> SEQ ID NO 16
<211> LENGTH: 2586
<212> TYPE: DNA
<213> ORGANISM: Artificial Sequence
<220> FEATURE:
<223> OTHER INFORMATION: Cre-1-kanMX fragment

<400> SEQUENCE: 16
gcaatttcgg ctatacgtaa cagggtgtta taagcaatcc ccagaaatgc cagattacgt      60
atatcctggc agcgatcgct attttccatg agtgaacgaa cctggtcgaa atcagtgcgt     120
tcgaacgcta gagcctgttt tgcacgttca ccggcatcaa cgttttcttt tcggatccgc     180
cgcataacca gtgaaacagc attgctgtca cttggtcgtg gcagcccgga ccgacgatga     240
agcatgttta gctggcccaa atgttgctgg atagtttttta ctgccagacc gcgcgcctga     300
agatatagaa gataatcgcg aacatcttca ggttctgcgg gaaaccattt ccggttattc     360
aacttgcacc atgccgccca cgaccggcaa acggacagaa gcattttcca ggtatgctca     420
gaaaacgcct ggcgatccct gaacatgtcc atcaggttct tgcgaacctc atcactcgtt     480
```

```
gcatcgaccg gtaatgcagg caaattttgg tgtacggtca gtaaattgga catttaacac      540
tcagataatg gttttaagta aagtgtacag gatcggctct gccccctcgac ggtatcgata     600 agcttgatat cgaattcctg cagcccgggg gatccactag ttctagaatc cggggttttt     660
tctccttgac gttaaagtat agaggtatat taacaatttt tgttgatac ttttattaca      720 tttgaataag aagtaataca aaccgaaaat gttgaaagta ttagttaaag tggttatgca     780 gttttttgcat ttatatatct gttaatagat caaaaatcat cgcttcgctg attaattacc    840
ccagaaataa ggctaaaaaa ctaatcgcat tatcatccta tggttgttaa tttgattcgt    900
tcatttgaag gtttgtgggg ccaggttact gccaattttt cctcttcata accataaaag    960
ctagtattgt agaatcttta ttgttcggag cagtgcggcg cgaggcacat ctgcgtttca    1020
ggaacgcgac cggtgaagac gaggacgcac ggaggagagt cttccttcgg agggctgtca   1080
cccgctcggc ggcttctaat ccgtactaga tttaaatgac atggaggccc agaatacct    1140 ccttgacagt cttgacgtgc gcagctcagg ggcatgatgt gactgtcgcc cgtacattta   1200
gcccatacat ccccatgtat aatcatttgc atccatacat tttgatggcc gcacggcgcg   1260
aagcaaaaat tacggctcct cgctgcagac ctgcgagcag ggaaacgctc ccctcacaga   1320
cgcgttgaat tgtccccacg ccgcgcccct gtagagaaat ataaaggtt aggatttgcc    1380 actgaggttc ttcttttcata tacttccttt taaaatcttg ctaggataca gttctcacat   1440
cacatccgaa cataaacaac catgggtaag gaaaagactc acgtttcgag gccgcgatta   1500
aattccaaca tggatgctga tttatatggg tataaatggg ctcgcgataa tgtcgggcaa   1560
tcaggtgcga caatctatcg attgtatggg aagcccgatg cgccagagtt gtttctgaaa    1620
catggcaaag gtagcgttgc caatgatgtt acagatgaga tggtcagact aaactggctg    1680
acggaattta tgcctcttcc gaccatcaag catttttatcc gtactcctga tgatgcatgg    1740
ttactcacca ctgcgatccc cggcaaaaca gcattccagg tattagaaga atatcctgat    1800
tcaggtgaaa atattgttga tgcgctggca gtgttcctgc gccggttgca ttcgattcct    1860
gtttgtaatt gtccttttaa cagcgatcgc gtatttcgtc tcgctcaggc gcaatcacga    1920
atgaataacg gtttggttga tgcgagtgat tttgatgacg agcgtaatgg ctggcctgtt    1980
gaacaagtct ggaaagaaat gcataagctt ttgccattct caccggattc agtcgtcact    2040
catggtgatt tctcacttga taaccttatt tttgacgagg ggaaattaat aggttgtatt    2100
gatgttggac gagtcggaat cgcagaccga taccaggatc ttgccatcct atggaactgc    2160
ctcggtgagt tttctccttc attacagaaa cggctttttc aaaaatatgg tattgataat    2220
cctgatatga ataaattgca gtttcatttg atgctcgatg agttttttcta atcagtactg    2280 acaataaaaa gattcttgtt ttcaagaact tgtcatttgt atagtttttt tatattgtag    2340
ttgttctatt ttaatcaaat gttagcgtga tttatatttt ttttcgcctc gacatcatct    2400
gcccagatgc gaagttaagt gcgcagaaag taatatcatg cgtcaatcgt atgtgaatgc    2460
tggtcgctat actgatttaa atataacttc gtatagcata cattatacga acggtactcg    2520
aggtcgacgt tgacttttg ttatgttatg ctaagagttt tctctcaatt gttaggtatt   2580
tgggtg                                                                2586
```

<210> SEQ ID NO 17
<211> LENGTH: 79
<212> TYPE: DNA
<213> ORGANISM: Artificial Sequence
<220> FEATURE:

<223> OTHER INFORMATION: Primer DBC-03756

<400> SEQUENCE: 17

```
cacccaaata cctaacaatt gagagaaaac tcttagcata acataacaaa aagtcaacgt    60
cgacctcgag taccgttcg                                                 79
```

<210> SEQ ID NO 18
<211> LENGTH: 21
<212> TYPE: DNA
<213> ORGANISM: Artificial Sequence
<220> FEATURE:
<223> OTHER INFORMATION: Primer DBC-03373

<400> SEQUENCE: 18

```
gcaatttcgg ctatacgtaa c                                              21
```

<210> SEQ ID NO 19
<211> LENGTH: 1274
<212> TYPE: DNA
<213> ORGANISM: Artificial Sequence
<220> FEATURE:
<223> OTHER INFORMATION: Cre-2 fragment

<400> SEQUENCE: 19

```
cgttcactca tggaaaatag cgatcgctgc caggatatac gtaatctggc atttctgggg    60
attgcttata acaccctgtt acgtatagcc gaaattgcca ggatcagggt aaagatatc    120 tcacgtactg acggtgggag aatgttaatc catattggca gaacgaaaac gctggttagc   180
accgcaggtg tagagaaggc acttagcctg ggggtaacta aactggtcga gcgatggatt   240
tccgtctctg gtgtagctga tgatccgaat aactacctgt tttgccgggt cagaaaaaat   300
ggtgttgccg cgccatctgc caccagccag ctatcaactc gcgccctgga agggattttt   360
gaagcaactc atcgattgat ttacggcgct aaggatgact ctggtcagag atacctggcc   420
tggtctggac acagtgcccg tgtcggagcc gcgcgagata tggcccgcgc tggagtttca   480
ataccggaga tcatgcaagc tggtggctgg accaatgtaa atattgtcat gaactatatc   540
cgtaccctgg atagtgaaac aggggcaatg gtgcgcctgc tggaagatgg cgattagcca   600
ttaacgcgta atgattgct ataattattt gatatttatg gtgacatatg agaaaggatt    660
tcaacatcga cggaaaatat gtagtgctgt ctgtaagcac taatattcag tcgccagccg   720
tcattgtcac tgtaaagctg agcgatagaa tgcctgatat tgactcaata tccgttgcgt   780
ttcctgtcaa aagtatgcgt agtgctgaac atttcgtgat gaatgccacc gaggaagaag   840
cacggcgcgg ttttgcttaa agtgatgtct gagtttggcg aactcttggg taaggttgga   900
attgtcgacc tcgagtcatg taattagtta tgtcacgctt acattcacgc cctcccccca   960
catccgctct aaccgaaaag gaaggagtta gacaacctga agtctaggtc cctatttatt   1020
tttttatagt tatgttagta ttaagaacgt tatttatatt tcaaattttt ctttttttc    1080 tgtacagacg cgtgtacgca tgtaacatta tactgaaaac cttgcttgag aaggttttgg   1140
gacgctcgaa ggctttaatt tgcggccggt acataacttc gtataatgta tgctatacga   1200
acggtaggat ccggaaatag gacaaggatt aaccattaga actgccggca tttcctgaca   1260
agtatatata ttcg                                                     1274
```

<210> SEQ ID NO 20
<211> LENGTH: 21
<212> TYPE: DNA
<213> ORGANISM: Artificial Sequence

```
<220> FEATURE:
<223> OTHER INFORMATION: Primer DBC-03374

<400> SEQUENCE: 20
cgttcactca tggaaaatag c                                              21

<210> SEQ ID NO 21
<211> LENGTH: 82
<212> TYPE: DNA
<213> ORGANISM: Artificial Sequence
<220> FEATURE:
<223> OTHER INFORMATION: Primer DBC-03757

<400> SEQUENCE: 21
cgaatatata tacttgtcag gaaatgccgg cagttctaat ggttaatcct tgtcctattt    60
ccggatccta ccgttcgtat ag                                             82

<210> SEQ ID NO 22
<211> LENGTH: 29
<212> TYPE: DNA
<213> ORGANISM: Artificial Sequence
<220> FEATURE:
<223> OTHER INFORMATION: Primer DBC-03760

<400> SEQUENCE: 22
ggaaatgtaa aggataatga gtgagcata                                      29

<210> SEQ ID NO 23
<211> LENGTH: 30
<212> TYPE: DNA
<213> ORGANISM: Artificial Sequence
<220> FEATURE:
<223> OTHER INFORMATION: Primer DBC-03761

<400> SEQUENCE: 23
gctaaaagat gacgagtacc ttctaacggc                                     30

<210> SEQ ID NO 24
<211> LENGTH: 3449
<212> TYPE: DNA
<213> ORGANISM: Artificial Sequence
<220> FEATURE:
<223> OTHER INFORMATION: Product of DBC-03760 and DBC-03761 wild type
      ICL1

<400> SEQUENCE: 24
ggaaatgtaa aggataatga gtgagcatat aaaatggaag aaaaaataat aataggatta    60
tgtataaaat atcgattccc ttttgtagat ttcgagatct tcgaggagaa cttctagcac   120
gttgtttaca tatctaatgt tgtaacacgg cctttgttat cttgtgaata tatccatcac   180
ctacgtcgct tgaggtttcg tatcaaagaa agagagttca acataatca tacgtgtttc    240 actccaaatt tgatcacaaa tggccaccca ttatagcttg ttattattta cttcttcttg   300
agttcatttt attgaaagat gcccgctggg aacaaaacat aaataaaatt caagagtaca   360
atatagcgta gcatagttgc gagcaaggga aggcaacaca gttaaaatga caatgttaga   420
aggaaaaact aaatcaagct cccataggaa atttcttgtg tcagtaatat gtctcgagaa   480
aataataata attgaatcta tttattgaaa agtaaatatc tcgtaacccg gatgctttgg   540
gcggtcgggt tttgctactc gtcatccgat gagaaaaact gttcccttt gccccaggtt    600 tccattcatc cgagcgatca cttatctgac ttcgtcactt tttcatttca tccgaaacaa   660
tcaaaactga agccaatcac cacaaaatta acactcaacg tcatctttca ctaccctta    720
```

```
cagaagaaaa tatccatagt ccggactagc atcccagtat gtgactcaat attggtgcaa      780
aagagaaaag cataagtcag tccaaagtcc gcccttaacc aggcacatcg gaattcacaa      840
aacgtttctt tattatataa aggagctgct tcactggcaa aattcttatt atttgtcttg      900
gcttgctaat ttcatcttat cctttttttc ttttcacacc caaataccta acaattgaga      960
gaaaactctt agcataacat aacaaaaagt caacgaaaaa tgcctatccc cgttggaaat     1020
acgaagaacg attttgcagc tttacaagca aaactagatg cagatgctgc cgaaattgag     1080
aaatggtggt ctgactcacg ttggagtaag actaagagaa attattcagc cagagatatt     1140
gctgttagac gcgggacatt cccaccaatc gaatacccat cttcggtcat ggccagaaaa     1200
ttattcaagg tattagagaa gcatcacaat gagggtacag tctctaaaac tttcggtgcc     1260
ctagatcctg tccagatttc tcaaatggca aaatacttag acacaatcta tatttctggt     1320
tggcagtgtt catcaactgc ttccacctca aatgaacctg gtccagactt agctgattat     1380
ccaatggaca ccgttccaaa caaagtggaa catttgttca aggcccaatt gtttcacgac     1440
agaaaacaac tagaggcacg gtcaaaggct aaatctcagg aagaactcga tgagatgggt     1500
gccccaattg actacctaac accaattgtc gctgatgcag acgcaggcca cggcggttta     1560
accgcagtct tcaaattgac caagatgttc attgagcgtg gtgctgctgg gatccacatg     1620
gaagaccaga catctacaaa taagaaatgt gggcatatgg caggaagatg tgttataccc     1680
gttcaggaac atgttaacag attggtgact attagaatgt gtgctgatat catgcattct     1740
gacttaattg tcgttgctag gactgattca gaagcagcca cttttgattag ctcaaccatc     1800 gataccagag atcattattt cattgtcggt gccaccaatc caaatatcga gccatttgcc     1860
gaagttttaa atgatgccat catgagtggt gcatcaggac aagaactagc tgacattgaa     1920
caaaaatggt gtagagacgc tggactcaag ttattccatg aagccgtcat tgatgaaatt     1980
gaaagatcag ccctgtcaaa taagcaagaa ttgattaaga aattccactc taaagtgggt     2040
ccattgactg aaacatccca cagagaagcc aagaagctcg ctaaagaaat tcttggccac     2100
gaaattttct tcgactggga gctaccacgc gtaagggaag ggttgtaccg ttacagaggt     2160
gggacgcaat gttctatcat gagggcccgt gcatttgctc catatgctga tttggtatgg     2220
atggaatcta actacccaga cttccaacag gccaaggagt ttgcagaagg tgttaaagag     2280
aaattccctg accaatggct agcttacaac ttgtctccat cctttaactg gccaaaagcc     2340
atgtccgttg atgaacaaca caccttcatc caaaggctgg gtgatctagg ttacatctgg     2400
caatttatca cattggccgg tttacacact aacgctttag ctgtccataa cttctctcgt     2460
gactttgcca aggatgggat gaaagcttat gcccagaatg ttcagcagag ggaaatggac     2520
gatggtgttg atgtgttgaa acatcaaaaa tggtctggtg cggagtacat cgatgggtta     2580
ttgaagttag ctcaaggtgg tgttagcgca acagctgcta tgggaaccgg tgtcacagaa     2640
gatcaattca agaaaatgg cgtaaagaaa taggacaagg attaaccatt agaactgccg     2700
gcatttcctg acaagtatat atattcgtaa tctcaatgta tatttttttc atatataaac     2760
atgcgtactt aaaaacttaa actcatcgtt actgcagtac aatgttctct aatggcatct     2820
ctctaatggt actccaacta aagtcaacat tctctccgtg caagaatgcc tttctctagt     2880
tgcaaaaacg agtcaataaa catctttgat cgagtcgcct cattttgtt gactcggtga      2940 ctaaaatcag tgccatttct gtccatgcct cgtgcgcgaa tgattgaatc gaactaatcc     3000
cgaacacaat catagtatcg tatcgcccat tagtgccgtg agtgtacgcg aggcaaaagg     3060
```

```
caccatggaa aatattccct tagtcatctt ggaaatcatt gagactgtaa aggaactcgc    3120
aaacgggtaa ccgatattta ccccacctttt ggtcgagaaa ttccacctgt tcggcaattt    3180
ttgccgctct tctcaagagc aaaaggcgtt ttttttttctg acacgcctct tctctcgcat    3240
gccaaactca agcgtcctac atgcttttct catgaaagcc aagtgcggga tgaaaaacat    3300
aaaatgtgac aaatagtgcc acctcataat gtaatcgaga ggcaaaatta atcactttgt    3360
tctccctttt cttttttctg ggcgctcaaa gtgagatgct ttctgtagaa ataacatgg     3420 ccgttagaag gtactcgtca tcttttagc                                       3449
```

<210> SEQ ID NO 25
<211> LENGTH: 1812
<212> TYPE: DNA
<213> ORGANISM: Artificial Sequence
<220> FEATURE:
<223> OTHER INFORMATION: Product of DBC-03760 and DBC-03761 ICL1
       deletion and kanMX marker and Cre recombinase out-recombination

<400> SEQUENCE: 25

```
ggaaatgtaa aggataatga gtgagcatat aaaatggaag aaaaaataat aataggatta     60
tgtataaaat atcgattccc ttttgtagat ttcgaggagaa cttctagcac                120 gttgtttaca tatctaatgt tgtaacacgg cctttgttat cttgtgaata tatccatcac    180
ctacgtcgct tgaggtttcg tatcaaagaa agagagttca aacataatca tacgtgtttc    240
actccaaatt tgatcacaaa tggccaccca ttatagcttg ttattattta cttcttcttg    300
agttcatttt attgaaagat gcccgctggg aacaaaacat aaataaaatt caagagtaca    360
atatagcgta gcatagttgc gagcaaggga aggcaacaca gttaaaatga caatgttaga    420
aggaaaaact aaatcaagct cccataggaa atttcttgtg tcagtaatat gtctcgagaa    480
aataataata attgaatcta tttattgaaa agtaaatatc tcgtaacccg gatgctttgg    540
gcggtcgggt tttgctactc gtcatccgat gagaaaaact gttcccttttt gccccaggtt    600 tccattcatc cgagcgatca cttatctgac ttcgtcactt tttcatttca tccgaaacaa    660
tcaaaactga agccaatcac cacaaaatta acactcaacg tcatctttca ctacccttta    720
cagaagaaaa tatccatagt ccggactagc atcccagtat gtgactcaat attggtgcaa    780
aagagaaaag cataagtcag tccaaagtcc gcccttaacc aggcacatcg gaattcacaa    840
aacgtttctt tattatataa aggagctgct tcactggcaa aattcttatt atttgtcttg    900
gcttgctaat ttcatcttat ccttttttttc ttttcacacc caaataccta acaattgaga    960
gaaaactctt agcataacat aacaaaaagt caacgtaccg ttcgtataat gtatgctata   1020
cgaacggtag aaataggaca aggattaacc attagaactg ccggcatttc ctgacaagta   1080
tatatattcg taatctcaat gtatatttttt ttcatatata aacatgcgta cttaaaaact   1140
taaactcatc gttactgcag tacaatgttc tctaatggca tctctctaat ggtactccaa    1200
ctaaagtcaa cattctctcc gtgcaagaat gcctttctct agttgcaaaa acgagtcaat    1260
aaacatcttt gatcgagtcg cctcattttt gttgactcgg tgactaaaat cagtgccatt    1320
tctgtccatg cctcgtgcgc gaatgattga atcgaactaa tcccgaacac aatcatagta   1380
tcgtatcgcc cattagtgcc gtgagtgtac gcgaggcaaa aggcaccatg gaaaatattc    1440
ccttagtcat cttggaaatc attgagactg taaaggaact cgcaaacggg taaccgatat    1500
ttaccccacc tttggtcgag aaattccacc tgttcggcaa ttttttgccgc tcttctcaag    1560 agcaaaaggc gttttttttt ctgacacgcc tcttctctcg catgccaaac tcaagcgtcc    1620
```

```
tacatgctttt tctcatgaaa gccaagtgcg ggatgaaaaa cataaaatgt gacaaatagt      1680
gccacctcat aatgtaatcg agaggcaaaa ttaatcactt tgttctccct tttcttttt       1740 ctgggcgctc aaagtgagat gctttctgta gaaaataaca tggccgttag aaggtactcg      1800 tcatcttta gc                                                           1812
```

<210> SEQ ID NO 26
<211> LENGTH: 5787
<212> TYPE: DNA
<213> ORGANISM: Artificial Sequence
<220> FEATURE:
<223> OTHER INFORMATION: Product of primer DBC-07072 and primer
      DBC-08586
<220> FEATURE:
<221> NAME/KEY: misc_feature
<222> LOCATION: (3716)..(3716)
<223> OTHER INFORMATION: n is a, c, g, or t

<400> SEQUENCE: 26

```
tggcaagtac tccgtacatc aggttacata catactgatt ctctaaagct agataacgaa       60
taggattctc gcacagacag tatgtgtctc ttgtctgtca gatgataagc agatgaacaa      120
agaaagtata actgcttact acctacatgc cgacatttag tcgattcctt tcggagaatt      180
tattatggat tattaatagc atacccccggg attggcagaa ggggtaaaag gtccgactag    240
acaaggatat ccatacagta cataccgttg atacagatcg aatcacatgc atactgctga     300
tggtgtgatg aatccttgaa ttagacaatc atccagacct gtctggacag agatcctggc     360
actgaacaat ccactcattg ctatctatcg gtactctgta cctgttttcag ctgaagcttg    420 ccaatcgcag actgccatct gcaactgatc agcgccagga tgcaggtcat gatacccag      480 cgttgttccc gaggtgtcat tgcttaaacg cgttaaccag tgtgctaaac gtgctaaacg     540
tgctaaatgc taaactgctg atgctatgca gctgcatcgc cgaatctgga gaatgcagat    600
cacctgccga cggcgggctc cgggcacgtg cacgggggac cccgtaggac agaaacgtcc     660
atcgagagta cggagtacgg agtattacaa gaccctgtcc atcagaccct gtccatcgtc     720
attgccaaga tctctcattg tttgctgttt catgctcgga tcaccagtgg acagcaatgc     780
cccgtgaaca gcaagccgca tgctggtccg tgtcttgtcc gtgtgccgat gtagtattgc    840
taacgagacc cagaatggca tcaatgacgt tgcggatgac agaatgaggg ggatcatcag    900
tacgtctgct atcaggatga ttatcctacg gagtatttac tcagctgaag acaggaacaa     960
gatcgtctga tggatgaggc ccacggccag ccagcacaga ctccgtactc ttcagtcttc    1020
tggatttgac cgttcgacgg cgcctccgac gtagcatctc gctagcctga tccttggctg    1080
cgcctatcgt cggctcatgc ccctgttgat gacggggaag tggagcggcg ccgcgataag   1140
gttgccttgc taatttagcg cctgcacgct ccagccaaaa agaccaatat tgaggtcgat    1200
cgtctcccct ggctccgtgc tgctggcctg cgatcgccgg cgcgatcata ccctgcaatc    1260
acgccgccag cctatcacag accatgcggt ccttgcacca tctgggagct cgagctctcc    1320
tgactgccgt cggggcgtca atgcgtccgg agcctccgac gagggcctct gctcctcgtc    1380
tgtcctactg gagcttgtcc gtcagacgtc gcatcctgag ccgtgtgctg atatcgccat    1440
ggctctgacg tgatcgactg cgagcggccg gcgaggctat aagaagccgc aacttgctgc    1500
tcgaagtacc gtctcccatc catcgatcag acagtcagca gtcctcactc agtcagtcct    1560
cagtttaatt aataccgttc gtatagcata cattatacga agttatgcg cgccagacag    1620 ctctggcggc tctgaggtgc agtggatgat tattaatccg ggaccggccg ccctccgcc     1680
```

```
ccgaagtgga aaggctggtg tgcccctcgt tgaccaagaa tctattgcat catcggagaa   1740
tatggagctt catcgaatca ccggcagtaa gcgaaggaga atgtgaagcc agggtgtat    1800
agccgtcggc gaaatagcat gccattaacc taggtacaga agtccaattg cttccgatct   1860
ggtaaaagat tcacgagata gtaccttctc cgaagtaggt agagcgagta cccggcgcgt   1920
aagctcccta attggcccat ccggcatctg tagggcgtcc aaatatcgtg cctctcctgc   1980
tttgcccggt gtatgaaacc ggaaaggccg ctcaggagct ggccagcggc gcagaccggg   2040
aacacaagct ggcagtcgac ccatccggtg ctctgcactc gacctgctga ggtccctcag   2100
tccctggtag gcagctttgc cccgtctgtc cgcccggtgt gtcggcgggg ttgacaaggt   2160
cgttgcgtca gtccaacatt tgttgccata ttttcctgct ctccccacca gctgctcttt   2220
tcttttctct ttcttttccc atcttcagta tattcatctt cccatccaag aacctttatt   2280
tcccctaagt aagtactttg ctacatccat actccatcct tcccatccct tattcctttg   2340
aacctttcag ttcgagcttt cccacttcat cgcagcttga ctaacagcta ccccgcttga   2400
gcagacatca ccatgcctga actcaccgcg acgtctgtcg agaagtttct gatcgaaaag   2460
ttcgacagcg tctccgacct gatgcagctc tcggagggcg aagaatctcg tgctttcagc   2520
ttcgatgtag gagggcgtgg atatgtcctg cgggtaaata gctgcgccga tggtttctac   2580
aaagatcgtt atgtttatcg gcactttgca tcggccgcgc tcccgattcc ggaagtgctt   2640
gacattgggg aattcagcga gagcctgacc tattgcatct cccgccgtgc acagggtgtc   2700
acgttgcaag acctgcctga aaccgaactg cccgctgttc tgcagccggt cgcggaggcc   2760
atggatgcga tcgctgcggc cgatcttagc cagacgagcg ggttcggccc attcggaccg   2820
caaggaatcg gtcaatacac tacatggcgt gatttcatat gcgcgattgc tgatccccat   2880
gtgtatcact ggcaaactgt gatggacgac accgtcagtg cgtccgtcgc gcaggctctc   2940
gatgagctga tgctttgggc cgaggactgc cccgaagtcc ggcacctcgt gcacgcggat   3000
ttcggctcca acaatgtcct gacgacaat ggccgcataa cagcggtcat tgactggagc   3060
gaggcgatgt tcggggattc ccaatacgag gtcgccaaca tcttcttctg gaggccgtgg   3120
ttggcttgta tggagcagca gacgcgctac ttcgagcgga ggcatccgga gcttgcagga   3180
tcgccgcggc tccgggcgta tatgctccgc attggtcttg accaactcta tcagagcttg   3240
gttgacggca atttcgatga tgcagcttgg gcgcagggtc gatgcgacgc aatcgtccga   3300
tccggagccg ggactgtcgg gcgtacacaa atcgcccgca gaagcgcggc cgtctggacc   3360
gatggctgtg tagaagtact cgccgatagt ggaaaccgac gccccagcac tcgtccgagg   3420
gcaaaggaat agagtagatg ccgaccgcgg gatccactta acgttactga aatcatcaaa   3480
cagcttgacg aatctggata taagatcgtt ggtgtcgatg tcagctccgg agttgagaca   3540
aatggtgttc aggatctcga taagatacgt tcatttgtcc aagcagcaaa gagtgccttc   3600
tagtgattta atagctccat gtcaacaaga ataaaacgcg ttttcgggtt tacctcttcc   3660
agatacagct catctgcaat gcattaatgc attgactgca acctagtaac gccttncagg   3720
ctccggcgaa gagaagaata gcttagcaga gctattttca ttttcgggag acgagatcaa   3780
gcagatcaac ggtcgtcaag agacctacga gactgaggaa tccgctcttg gctccacgcg   3840
actatatatt tgtctctaat tgtactttga catgctcctc ttctttactc tgatagcttg   3900
actatgaaaa ttccgtcacc agccctgggt tcgcaaagat aattgcatgt ttcttccttg   3960
aactctcaag cctacaggac acacattcat cgtaggtata aacctcgaaa tcattcctac   4020
taagatggta tacaatagta accatgcatg gttgcctagt gaatgctccg taacacccaa   4080
```

```
tacgccggtc ctggaagtgc gttgatcatt attccccgaa aatgtagtac ccagtaagtg     4140
gtctagcggt ggctatggta ggacatctat gcctaagctg gagttctcat tgaacgtgta     4200
ccggccgatt gccctaaact ctgattgaga gccggaaacc tcatctacct gatgctcagg     4260
ggccatccaa tagcttccga tagcattaca gacagatgga ctcgtcttgg cccacgggtc     4320
tagaacagtc gccggaactg cctctatttg aaacggagct gaaccatgat acttaagcgt     4380
gccaagcggc gccgtttccc actggaacaa ggagcaatag aattctgcag agattcttca     4440
ttcaggctat tcagcaattc ggtttgtgga gcggatcggg gtccactggg tttagtctgg     4500 ggttttctt tgcccgcatg ggctctagca catgcacagc ttgcagttgc tgctacgcta     4560
tctgggaaaa cgaatggcta ttcaggagtt tataaccaaa agagccggaa acaggctgat     4620
tgccctctca cggggagacg ttgtacttct gatccagagg ctattaaccg gacactacct     4680
ataaaggagg tagcattcct ttctgtccgg ctcccagatt ccaacaaccc aactgacagg     4740
atcagcacaa tgcaggaatt ccaccatgtc caatttactg accgtacacc aaaatttgcc     4800
tgcattaccg gtcgatgcaa cgagtgatga ggttcgcaag aacctgatgg acatgttcag     4860
ggatcgccag gcgttttctg agcatacctg gaaaatgctt ctgtccgttt gccggtcgtg     4920
ggcggcatgg tgcaagttga ataaccggaa atggtttccc gcagaacctg aagatgttcg     4980
cgattatctt ctatatcttc aggcgcgcgg tctggcagta aaaactatcc agcaacattt     5040
gggccagcta aacatgcttc atcgtcggtc cgggctgcca cgaccaagtg acagcaatgc     5100
tgtttcactg gttatgcggc ggatccgaaa agaaaacgtt gatgccggtg aacgtgcaaa     5160
acaggctcta gcgttcgaac gcactgattt cgaccaggtt cgttcactca tggaaaatag     5220
cgatcgctgc caggatatac gtaatctggc atttctgggg attgcttata caccctgtt     5280 acgtatagcc gaaattgcca ggatcagggt taaagatatc tcacgtactg acggtgggag     5340
aatgttaatc catattggca gaacgaaaac gctggttagc accgcaggtg tagagaaggc     5400
acttagcctg ggggtaacta aactggtcga gcgatggatt tccgtctctg tgtgagctga     5460
tgatccgaat aactacctgt tttgccgggt cagaaaaaat ggtgttgccg cgccatctgc     5520
caccagccag ctatcaactc gcgccctgga agggatttt gaagcaactc atcgattgat     5580
ttacggcgct aaggatgact ctggtcagag atacctggcc tggtctggac acagtgcccg     5640
tgtcggagcc gcgcgagata tggcccgcgc tggagtttca ataccggaga tcatgcaagc     5700
tggtggctgg accaatgtaa atattgtcat gaactatatc cgtaacctgg atagtgaaac     5760
aggggcaatg gtgcgcctgc tggaaga                                         5787

<210> SEQ ID NO 27
<211> LENGTH: 2357
<212> TYPE: DNA
<213> ORGANISM: Artificial Sequence
<220> FEATURE:
<223> OTHER INFORMATION: Product of primer DBC-08585 and primer
      DBC-04415

<400> SEQUENCE: 27
ctgcattacc ggtcgatgca acgagtgatg aggttcgcaa gaacctgatg gacatgttca      60
gggatcgcca ggcgttttct gagcatacct ggaaaatgct tctgtccgtt tgccggtcgt     120
gggcggcatg gtgcaagttg aataaccgga atggtttccc gcagaacct gaagatgttc     180 gcgattatct ctatatcttc aggcgcgcg gtctggcagt aaaaactatc cagcaacatt     240
tgggccagct aaacatgctt catcgtcggt ccgggctgcc acgaccaagt gacagcaatg     300
```

```
ctgtttcact ggttatgcgg cggatccgaa agaaaacgt tgatgccggt gaacgtgcaa      360
aacaggctct agcgttcgaa cgcactgatt tcgaccaggt tcgttcactc atggaaaata      420
gcgatcgctg ccaggatata cgtaatctgg catttctggg gattgcttat aacaccctgt      480
tacgtatagc cgaaattgcc aggatcaggg ttaaagatat ctcacgtact gacggtggga      540
gaatgttaat ccatattggc agaacgaaaa cgctggttag caccgcaggt gtagagaagg      600
cacttagcct gggggtaact aaactggtcg agcgatggat ttccgtctct ggtgtagctg      660
atgatccgaa taactacctg ttttgccggg tcagaaaaaa tggtgttgcc gcgccatctg      720
ccaccagcca gctatcaact cgcgcccctgg aagggatttt tgaagcaact catcgattga      780
tttacggcgc taaggatgac tctggtcaga gatacctggc ctggtctgga cacagtgccc      840
gtgtcggagc cgcgcgagat atggcccgcg ctggagtttc aataccggag atcatgcaag      900
ctggtggctg gaccaatgta aatattgtca tgaactatat ccgtaacctg gatagtgaaa      960
caggggcaat ggtgcgcctg ctggaagatg gcgattagag ttctgtagcg aagtcaggac     1020
ctttgtccgc gcttccttga tcctgcacgg ggctgccgtc atctctggtt tctgatatgg     1080
tattcagcta tactgtcact cgaagtccta taactctctt actagcaata tgcttagcca     1140
agaactatat caggagagtt ttactaaaca ggatctctca ataacatgga gtagcctggc     1200
aattataaat ctagtattaa atctagtact aactcgatag atatagggct tttctggcga     1260
atgcctgtat ggtagctgga actcgcactg ctgcaggaat aacttcgtat agcatacatt     1320
atacgaacgg taatttaaat gcggccgcgt ttaaacctgc aggggtaccc taattactga     1380
gcacgtgctc catggtatgg gaagtggaga cgttgctata tatattgact gtcgggctat     1440
tgttcacggc gtagaagcta gacgctttgt ctatgtggcc ttcactaaag accgtgactc     1500
tgcccagtct tccccccttc gaggacctgg tattagccaa acccaccacc aaacctaaca     1560
aagatcatcg tgacattgaa gtcactctag gtactgctgg cgctgattac agtggctcaa     1620
ttcgaacatt tcaacagcac ataagggaag ggtcgcttca cttgctacct tgatacgaaa     1680
gcagccacgc ccaacactta tagggtgac aaccatcggc atgctgggtt atctactata     1740
tctcctgatt ctgtggatcc tggagatcga tctggtacac taatctacta caatgcatgt     1800
gaagtaggga taggcaagca tccactctcc atactcacat gacaataaac cgttgtagat     1860
ccctccagat ccgacgacag cattatccgc atactgaatt acgatgtgat ggtttggcct     1920
ctgcaaactt taacatccga tagtctggat gatctgggct ggactcgcct gaggtatcca     1980
tgacaagtca gcggagttat ttagtcagcg gggataagct gacggggggct ccgctatctc     2040 cccgatccgg caattgggct agatcggttg catcttcatc cacgatccac ttgcggatca     2100
acgtggctga tcggatgccc tgaagacaat agatccgctg acacatccca caatggcccc     2160
gttcattggt ggtcgtgctt caggcaccct taacggcttc tactcttgcg agatccgatg     2220
gacaactagg ctgaaccctg ctccataaac ttcccggttc atactaagat ccggacccga     2280
gtatacgcac agcctaagtc aacccaattt gcatgctagc aagctttgta tgctgagcca     2340
tggaagccga tccggtt                                                    2357
```

<210> SEQ ID NO 28  
<211> LENGTH: 20  
<212> TYPE: DNA  
<213> ORGANISM: Artificial Sequence  
<220> FEATURE:  
<223> OTHER INFORMATION: Primer DBC-07072

```
<400> SEQUENCE: 28
tggcaagtac tccgtacatc                                              20

<210> SEQ ID NO 29
<211> LENGTH: 22
<212> TYPE: DNA
<213> ORGANISM: Artificial Sequence
<220> FEATURE:
<223> OTHER INFORMATION: Primer DBC-08586

<400> SEQUENCE: 29
tcttccagca ggcgcaccat tg                                           22

<210> SEQ ID NO 30
<211> LENGTH: 22
<212> TYPE: DNA
<213> ORGANISM: Artificial Sequence
<220> FEATURE:
<223> OTHER INFORMATION: Primer DBC-08585

<400> SEQUENCE: 30
ctgcattacc ggtcgatgca ac                                           22

<210> SEQ ID NO 31
<211> LENGTH: 25
<212> TYPE: DNA
<213> ORGANISM: Artificial Sequence
<220> FEATURE:
<223> OTHER INFORMATION: Primer DBC-04415

<400> SEQUENCE: 31
aaccggatcg gcttccatgg ctcag                                        25
```

RECOMBINATION SYSTEM

CROSS REFERENCE TO RELATED APPLICATIONS

This application is a § 371 National Stage Application of PCT/EP2013/055047, filed Mar. 12, 2013, which claims priority to EP 12159094.7, filed Mar. 12, 2012.

BACKGROUND

Field of the Invention

The present invention relates to a method for carrying out recombination at a target locus.

Description of Related Art

Different cell types may be used for different industrial purposes. For example: mammalian cell lines are used for antibody production; fungal cells are preferred organisms for production of polypeptides and secondary metabolites; bacterial cells are preferred for small metabolite and antibiotic production; and plant cells are preferred for taste and flavor compounds.

Recombinant techniques are widely employed for optimization of the productivity of such cells and/or the processes in which they are used. This can involve a multitude of options, including, but not limited to over expression of a gene of interest, deletion or inactivation of competing pathways, changing compartmentalization of enzymes, increasing protein or metabolite secretion, increasing organelle content and the like.

In the case of filamentous fungi, the limited availability of selectable markers complicates the construction of new cell lines. Typically, target sequences are altered in vitro to create mutant alleles with inserted antibiotic resistance markers. However, regulatory authorities in most countries object to the use of antibiotic resistance markers in view of the potential risks of spreading resistance genes to the biosphere from large-scale use of production strains carrying such genes. In addition, there is a limited number of selectable markers suitable for use in filamentous fungi. Accordingly, selectable marker genes may need to be removed so that production strains may be used commercially and/or so that the same marker gene may be recycled for use in sequential strain modification.

SUMMARY

The invention concerns a method for carrying out recombination at a target locus, or target loci, for example within a target genome. The recombination method of the invention results in alteration of the target locus, for example the insertion of nucleic acid sequence at the target locus. The method may be carried out such that insertion of new sequence at the target locus is accompanied by removal of existing sequence from the target locus. That is to say, the method may be used to substitute a sequence at the target locus with an alternative sequence. The method may conveniently be carried out in vivo in a host cell.

Typically, when carried out in vivo, the method of the invention is not carried out on a human or animal cell. That is to say, the method of the invention is not typically carried out in the form of a method of treatment. The method of the invention may be carried out in an ex vivo or in vitro format. The terms ex vivo or in vitro should be understood to encompass methods carried out on microorganisms (both on whole living cells or on non-cellular material), but to exclude methods carried out on humans or animals.

The method is typically carried out such that at least part of the sequence inserted at the target locus is subsequently removed. If the method is carried out such that substitution of a sequence occurs at the target locus, followed by removal of the inserted sequence, the result may be deletion of sequence from the target locus.

Accordingly, the method of the invention may be carried out to achieve alteration of, the sequence of, the target locus. Such alteration may be, for example addition of new sequence, replacement of existing sequence and/or deletion/removal of existing sequence.

Typically, the invention is carried out in vivo in a host cell. The host cell may, preferably, be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

According to the invention, there is thus provided a method for carrying out recombination at a target locus, which method comprises:

providing two or more nucleic acids which, when taken together, comprise: (a) sequences capable of homologous recombination with sequences flanking the target locus; (b) two or more site-specific recombination sites; and (c) a sequence encoding a recombinase which recognizes the site-specific recombination sites, wherein the two or more nucleic acids are capable of homologous recombination with each other so as to give rise to a single nucleic acid, and wherein at least two of the two or more nucleic acids each comprise a sequence encoding a non-functional portion of the recombinase; and recombining the said two or more nucleic acids with each other and with the sequences flanking the target locus so that a contiguous nucleic acid sequence encoding a functional recombinase is inserted at the target locus, said recombinase-encoding sequence being flanked by at least two site-specific recombination sites and the said site-specific recombination sites being flanked by the sequences capable of homologous recombination with sequences flanking the target locus.

BRIEF DESCRIPTION OF SEQUENCE LISTING

Figure 1:
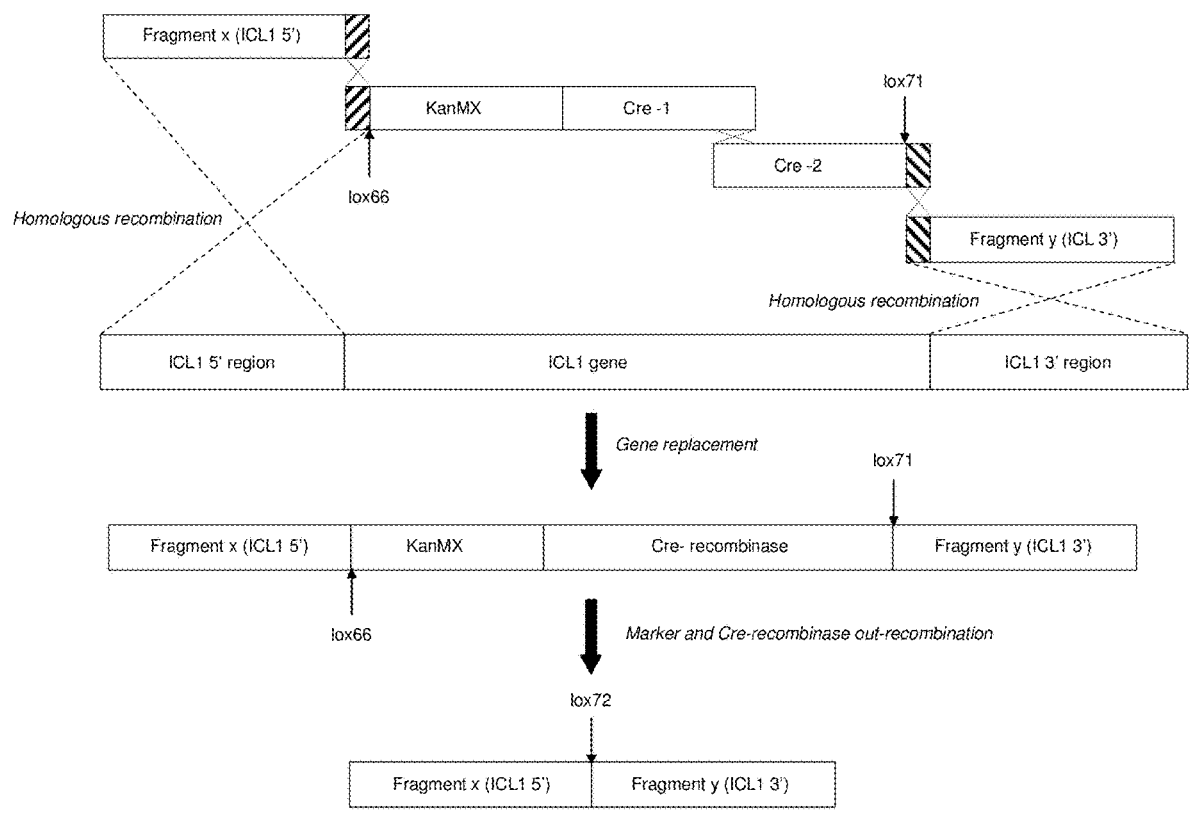
FIG. 1 sets out the principle of ICL1 removal by direct integration and in vivo recombination of split-cre recombinase construct. Expression of Cre-recombinase is regulated by the GAL1 promoter.

SEQ ID No: 1 sets out the nucleic acid sequence of the Cre-1 synthetic fragment.
SEQ ID No: 2 sets out the nucleic acid sequence of the Cre-2 synthetic fragment.
SEQ ID No: 3 sets out the complete nucleic acid sequence of pMA Cre1.
SEQ ID No: 4 sets out the complete nucleic acid sequence of pMA Cre2 (pSUC225).
SEQ ID No: 5 sets out the complete nucleic acid sequence of pUG7-EcoRV.
SEQ ID No: 6 sets out the nucleic acid sequence of primer DBC-02738.
SEQ ID No: 7 sets out the nucleic acid sequence of primer DBC-02739.
SEQ ID No: 8 sets out the nucleic acid sequence of the pCR-Blunt II-TOPO vector with kanMX marker PCR fragment.
SEQ ID No: 9 sets out the nucleic acid sequence of pSUC227.
SEQ ID No: 10 sets out the nucleic acid sequence of the 5' flanking fragment upstream of the ICL1 gene.
SEQ ID No: 11 sets out the nucleic acid sequence of primer DBC-03754.
SEQ ID No: 12 sets out the nucleic acid sequence of primer DBC-03755.
SEQ ID No: 13 sets out the nucleic acid sequence of the 3' flanking fragment downstream of the ICL1 gene.
SEQ ID No: 14 sets out the nucleic acid sequence of primer DBC-03758.
SEQ ID No: 15 sets out the nucleic acid sequence of primer DBC-03759.
SEQ ID No: 16 sets out the nucleic acid sequence of the "Cre-1-kanMX" fragment.
SEQ ID No: 17 sets out the nucleic acid sequence of primer DBC-03756.
SEQ ID No: 18 sets out the nucleic acid sequence of primer DBC-03373.
SEQ ID No: 19 sets out the nucleic acid sequence of the Cre-2 fragment.
SEQ ID No: 20 sets out the nucleic acid sequence of primer DBC-03374.
SEQ ID No: 21 sets out the nucleic acid sequence of primer DBC-03757.
SEQ ID No: 22 sets out the nucleic acid sequence of primer DBC-03760.
SEQ ID No: 23 sets out the nucleic acid sequence of primer DBC-03761.
SEQ ID No: 24 sets out the nucleic acid sequence of the product of DBC-03760 and DBC-03761 wild type ICL1.
SEQ ID No: 25 sets out the nucleic acid sequence of the product of DBC-03760 and DBC-03761 ICL1 deletion and kanMX marker and Cre recombinase out-recombination.
SEQ ID No: 26 sets out the nucleic acid sequence of the product of primer DBC-07072 and primer DBC-08586
SEQ ID No: 27 sets out the nucleic acid sequence of the product of primer DBC-08585 and primer DBC-04415
SEQ ID No: 28 sets out the nucleic acid sequence of primer DBC-07072
SEQ ID No: 29 sets out the nucleic acid sequence of primer DBC-08586
SEQ ID No: 30 sets out the nucleic acid sequence of primer DBC-08585
SEQ ID No: 31 sets out the nucleic acid sequence of primer DBC-04415

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The method according to the invention is one for carrying out recombination at a target locus. Recombination refers to a process in which a molecule of nucleic acid is broken and then joined to a different one. The recombination process of the invention typically involves the artificial and deliberate recombination of disparate nucleic acid molecules, which may be from the same or different organism, so as to create recombinant nucleic acids.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

The method of the invention relies on a combination of homologous recombination and site-specific recombination.

"Homologous recombination" refers to a reaction between nucleotide sequences having corresponding sites containing a similar nucleotide sequence (i.e., homologous sequences) through which the molecules can interact (recombine) to form a new, recombinant nucleic acid sequence. The sites of similar nucleotide sequence are each referred to herein as a "homologous sequence". Generally, the frequency of homologous recombination increases as the length of the homology sequence increases. Thus, while homologous recombination can occur between two nucleic acid sequences that are less than identical, the recombination frequency (or efficiency) declines as the divergence between the two sequences increases. Recombination may be accomplished using one homology sequence on each of two molecules to be combined, thereby generating a "single-crossover" recombination product. Alternatively, two homology sequences may be placed on each of two molecules to be recombined. Recombination between two homology sequences on the donor with two homology sequences on the target generates a "double-crossover" recombination product.

If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule.

"Site-specific recombination", also known as conservative site-specific recombination, is a type of recombination in which nucleic acid strand exchange takes place between segments possessing only a limited degree of sequence homology. Site-specific recombinase enzymes perform rearrangements of nucleic acid segments by recognizing and binding to short DNA sequences (sites), at which they cleave the DNA backbone, exchange the two DNA helices involved and rejoin the DNA strands. In some site-specific recombination systems having just a recombinase enzyme together with the recombination sites is enough to perform all these reactions, in some other systems a number of accessory proteins and accessory sites may also needed.

The method may be use to carry out recombination at a target locus resulting in modification of that target locus. Accordingly, the invention may be used to add, delete or otherwise change a target locus. The target locus may be a coding or a non-coding sequence. The method of the invention may be used so that such coding or non-coding sequence may be disrupted and/or partially or fully deleted and/or replaced. Thus, the method of the invention may be used to replace sequence at target locus, for example with a marker-encoding sequence.

Typically, the invention is carried out in vivo in a host cell (such as a cell of a microorganism). The host cell may, preferably, be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

Accordingly, the invention may be used, for example, in the optimization of the productivity of a host cell and/or the processes in which they are used. Alternatively, the invention may be used, for example, to introduce novel nucleic acids such that the host cell is rendered capable of producing a new compound of interest. The invention may be used sequentially, such that a plurality of novel nucleic acid sequences is introduced into the host cell, resulting in the introduction of an entirely new pathway metabolic pathway.

A target locus may be any nucleic sequence which is to be modified. Typically, the target locus may be a sequence within a genome (the complete genetic material of an organism), for example a locus on a chromosome. Such a chromosome could be a linear or a circular chromosome. However, the target locus could be extrachromosomal for example a locus on a plasmid, a minichromosome or artificial chromosome. The target locus may be located on a plasmid, a phage, or any other nucleic acid sequence which is able to replicate or be replicated in vitro or in a host cell The method of the invention may be carried out in vitro, ex vivo or in vivo.

The method of the invention comprises:
providing two or more nucleic acids which, when taken together, comprise: (a) sequences capable of homologous recombination with sequences flanking the target locus; (b) two or more site-specific recombination sites; and (c) a sequence encoding a recombinase which recognizes the site-specific recombination sites,
wherein the two or more nucleic acids are capable of homologous recombination with each other so as to give rise to a single nucleic acid, and
wherein at least two of the two or more nucleic acids each comprise a sequence encoding a non-functional portion of the recombinase; and
recombining the said two or more nucleic acids with each other and with the sequences flanking the target locus so that a contiguous nucleic acid sequence encoding a functional recombinase is inserted at the target locus, said recombinase-encoding sequence being flanked by at least two site-specific recombination sites and the said site-specific recombination sites being flanked by the sequences capable of homologous recombination with sequences flanking the target locus.

In the invention, at least two of the two or more nucleic acids each comprise a sequence encoding a non-functional portion of the recombinase. That is to say, the recombinase-encoding sequence is split across at least two of the two or more nucleic acids. Accordingly, the method may be referred to as a split-recombinase approach. Out-recombination of the nucleic acid sequence between the site-specific recombination sites may be carried out in vivo.

In the method of the invention, the in vivo recombination may be carried out in any suitable host cell, for example carried out in a prokaryotic or a eukaryotic cell.

In the method of the invention, recombination of the nucleic acids with each other and with the target locus is carried out in vivo.

In the method of the invention, two or more nucleic acids are provided. Taken together, the two or more nucleic acids provide: (a) sequences capable of homologous recombination with sequences flanking the target locus; (b) two or more site-specific recombination sites; and (c) a sequence encoding a recombinase which recognizes the site-specific recombination sites.

It is not intended that each of the two or more nucleic acids comprises the sequences set out in (a), (b) and (c). Rather, the sequences set out in (a), (b) and (c) must be comprised by the two or more nucleic acids when those nucleic acids are taken together as a group. Thus, one nucleic acid may comprise one or more of the sequences set out in (a), (b) and (c) and a second nucleic acid may comprise the other sequences set out in (a), (b) and (c). Typically, each of the two or more nucleic acids will comprise at least one of the sequences set out in (a), (b) and (c). However, additional nucleic acids may be provided which do not comprise at least one of the sequences set out in (a), (b) or (c).

One format for the method is set out in FIG. 1 in which four nucleic acids are used, but the skilled person will readily be able to conceive of further formats. The number of nucleic acids used in the method may be two, three, four, five, six or more.

Typically, the recombinase-encoding sequence will be split over two nucleic acid sequences (each of these two nucleic acid sequences encoding a non-functional portion of the recombinase, but when recombined the two will encode a functional recombinase). However, the recombinase-encoding sequence could be split of three, four or more nucleic acid sequences.

When the recombinase-encoding sequence is split over two nucleic acid sequences, each of those two sequences may typically also comprise a site-specific recombination site. This approach is shown is FIG. 1. Alternatively, the site-specific recombination sites may be provided on additional nucleic acid sequences capable of recombining with the nuclei acid sequences comprising the recombinase-encoding sequence.

In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus. In addition, at least two of the two or more nucleic acids each comprise a sequence encoding a non-functional portion of the recombinase.

Accordingly, in the method of the invention, the two or more nucleic acids are recombined with each other and with sequences flanking the target locus. In this way, a contiguous nucleic acid sequence encoding a functional recombinase may be inserted at the target locus together with at least two site-specific recombination sites. This functional recombinase-encoding sequence is typically inserted at the target locus such that it is flanked by at least two site-specific recombination sites. When the recombinase is expressed, the sequence situated between the site-specific recombination sites may be out-recombined. If the recombinase sequence is located between the site-specific recombination sites, it will be out-recombined. However, if the recombinase sequence lies outside the site-specific recombination sites, it will be retained at the target locus.

When recombination has taken place, the site-specific recombination sites and recombinase sequence will be flanked by the sequences capable of homologous recombination with sequences flanking the target locus.

The method of the invention may be carried out so that more than one, for example two, three, four, five or more target loci are targeted simultaneously. In such a method, the two or more nucleic acids, when taken together, comprise sequences capable of homologous recombination with sequences flanking two or more target loci. In this way, recombination of the said two or more nucleic acids with each other and with the sequences flanking the target loci results in the insertion of at least two site-specific recombination sites at each target loci. The two or more nucleic acids provided are such that a contiguous nucleic acid sequence encoding a functional recombinase is in inserted in at least one target locus, optionally located between at least two site-specific recombination sites. It is not necessary for other target loci to comprise a function recombinase-encoding sequence, but each target loci will comprise at least two site-specific recombination sites (which may be targeted by the recombinase). The method of the invention may though be carried out such that a recombinase-encoding sequence is inserted at all or some of the target loci.

Again, at each target locus, the said site-specific recombination sites and any recombinase-encoding sequence will be flanked by the sequences capable of homologous recombination with sequences flanking the target locus.

In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus.

In more detail, the two or more nucleic acids provided in the invention, when taken together, comprise sequences capable of homologous recombination two or more homologous recombination sites directed against the target locus. Where the method targets a single target locus typically, the two or more nucleic acids will provide two such sequences. These sequences are provided such that a contiguous nucleic acid sequence comprising the at least two or more nucleic acids (when recombined with each other) is inserted at the target locus via recombination with substantially homologous sequences which flank the target sequence.

It will be obvious to the skilled person that, in order to achieve homologous recombination via a double cross-over event, these flanking sequences need to be present at both sides/ends of the contiguous sequence resulting from recombination of the two or more nucleic acids and need to be substantially homologous to sequences at both sides of the target loci. Thus, the sequences capable of homologous recombination are typically provided such that they are located at the "5'" and "3'" ends of the nucleic acid sequence resulting from recombination of the two or more nucleic acids.

Moreover, the at least two nucleic acids provided according to the invention are capable of undergoing recombination with each other. Thus, the ends of the nucleic acids are conveniently designed such that this may take place and that the nucleic acids will be assembled in the desired orientation and order. Accordingly the sequence of the ends of a provided nucleic acid will be substantially homologous to the sequences of the ends of the nucleic acids with which it is intended to be recombined.

With the term "substantially homologous" as used in this invention is meant that a first nucleic acid sequence has a degree of identity with a second nucleic acid sequence with which it is to be recombined of at least about 70%, at least about 80%, preferably at least about 90%, over a region of not more than about 3 kb, preferably not more than about 2 kb, more preferably not more than about 1 kb, even more preferably not more than about 0.5 kb, even more preferably not more than about 0.2 kb, even more preferably not more than about 0.1 kb, such not more than about 0.05 kb, for example not more than about 0.03 kb. The degree of required identity may thereby depend on the length of the substantially homologous sequence. The shorter the homologous sequence, the higher the percentage homology may be.

In the invention, the two or more nucleic acids, taken together, comprise two or more site-specific recombination sites. These site-specific recombination sites are recognised by a recombinase which is encoded by the two or more nucleic acids, taken together. Critically, the two or more nucleic acids are provided so that at least two of the nucleic acids each comprise a sequence encoding a non-functional part of the recombinase-encoding sequence. When the two or more nucleic acids are recombined, this gives rise to a contiguous sequence encoding a functional recombinase.

The site-specific recombination sites and recombinase are selected such that the recombinase may target the site-specific recombination sites leading to out-recombination of sequence locate between the recombination sites.

The terms "recombinase" or "site-specific recombinase" or the like refers to enzymes or recombinases that recognize and bind to a short nucleic acid site or "site-specific recombinase site", i.e., a recombinase recognition site, and catalyze the recombination of nucleic acid in relation to these sites. These enzymes include recombinases, transposases and integrases.

The "site-specific recombinase site" or the like refers to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as lox66, lox71, loxP511, loxP514, lox486, lox4117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The site-specific recombination sites may be such that out-recombination following recombinase expression gives rise to a single mutant site-specific recombination site at the target locus which is not recognized by the recombinase. In particular, the lox sites may be lox66 and lox 71 (Albert, H., Dale, E. C., Lee, E., & Ow, D. W. (1995). Site-specific integration of DNA into wild-type and mutant lox sites placed in the plant genome. *Plant Journal*, 7(4), 649-659).

In addition to the recombinase, site-specific recombination site and sequences capable of homologous recombination with sequences flanking the target locus, a method may be carried out, wherein the two or more nucleic acids, taken together, comprise a marker-encoding sequence such that recombination of the two or more nucleic acids results in the said marker gene-encoding sequence being inserted at the target locus or loci. Such a marker-encoding sequence may be located between the at least two of the sequences capable of homologous recombination with sequences flanking the target locus or loci.

Typically, the method may be carried out so that a marker-encoding sequence is located between two or more site-specific recombination sites. In this way, the marker gene may be out-recombined on expression of the recombinase.

In this way, the method may be carried out in a repeated fashion with more than one cycle of recombination using the same marker. This approach may be further combined with the use of mutant site-specific recombination sites which cannot be targeted by the recombinase once the marker has out-recombined.

In a method of the invention, the two or more nucleic acids, taken together, may comprise two or more different marker-encoding sequences such that recombination of the two or more nucleic acids results in a different marker gene-encoding sequence being inserted at each target locus. This method may be carried out where sequences capable of homologous recombination with sequences flanking two or more target loci are provided. It is further possible, that one marker may be used to target at least two target loci and a different marker used to target a one or more further target loci.

In the method of the invention, the target locus may comprise a coding sequence which is disrupted and/or partially or fully deleted. Typically, the method adds new sequence at the target locus; this new sequence will typically replaceme sequence at the target locus.

As set out above, the replacement sequence may for instance confer a selectable phenotype when the recombination is carried out in vivo in a host cell. In that case, the replacement sequence comprises a selection marker. Preferentially, such a method is carried out so that the marker may be out-recombined on expression of the recombinase.

The replacement sequence may also be a modified version of the target sequence, for instance to provide for altered regulation of a sequence of interest or expression of a modified gene product with altered properties as compared to the original gene product.

The replacement sequence may also constitute additional copies of a sequence of interest being present in the genome of the host cell, to obtain amplification of that sequence of interest.

The replacement sequence may be a sequence homologous or heterologous to the host cell. It may be obtainable from any suitable source or may be prepared by custom synthesis.

The target sequence may be any sequence of interest. For instance, the target sequence may be a sequence of which the function is to be investigated by inactivating or modifying the sequence. The target sequence may also be a sequence of which inactivation, modification or over expression is desirable to confer on the host cell with a desired phenotype. Typically, the method of the invention will result in some nucleic acid sequence being removed at the target locus. However, the method of the invention may be used to insert sequence at the target locus without any sequence being lost from the target locus.

In the context of this disclosure, the terms "nucleic acid", "nucleic acid sequence", "polynucleotide", "polynucleotide sequence", "nucleic acid fragment", "isolated nucleic acid fragment" may be used interchangeably herein.

These terms encompass nucleotide sequences and the like. A nucleic acid may be a polymer of DNA or RNA that may be single- or double-stranded, that optionally contains synthetic, non-natural or altered nucleotide bases.

A nucleic acid in the form of a polymer of DNA may be comprised of one or more segments of cDNA, genomic DNA, synthetic DNA, or mixtures thereof.

The term "isolated nucleic acid" and the like refers to a nucleic acid that is substantially free from other nucleic acid sequences, such as and not limited to other chromosomal and extrachromosomal DNA and/or RNA. Isolated nucleic acids may be purified from a host cell in which they naturally occur.

Conventional nucleic acid purification methods known to skilled artisans may be used to obtain isolated nucleic acids. The term also embraces recombinant nucleic acids and chemically synthesized nucleic acids. Typically, each of the two or more nucleic acids suitable for use in the invention may be generated by any amplification process known in the art (e.g., PCR, RT-PCR and the like). The terms "amplify", "amplification", "amplification reaction", or "amplifying" as used herein refer to any in vitro process for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is typically different than a one-time, single primer extension step.

The two or more nucleic acids are typically introduced into a host cell so that the recombination events may take place. The two or more nucleic acids can be introduced into a host cell using various techniques which are well-known to those skilled in the art. Non-limiting examples of methods used to introduce heterologous nucleic acids into various organisms include; transformation, transfection, transduction, electroporation, ultrasound-mediated transformation, particle bombardment and the like. In some instances the addition of carrier molecules can increase the uptake of DNA in cells typically though to be difficult to transform by conventional methods. Conventional methods of transformation are readily available to the skilled person.

The procedures used to generate the two or more nucleic acids and to then introduce them into a host cell are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley Inter-Science, NY, 1995).

Furthermore, standard molecular biology techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid suitable for use in the method of the invention may be amplified using cDNA, mRNA or alternatively, genomic DNA, as a template and appropriate oligonucleotide primers according to standard PCR amplification techniques. The nucleic acid so amplified can be cloned into an appropriate vector if desirable and/or characterized by nucleic acid sequence analysis.

The method of the invention may be carried out such that the two or more nucleic acids are recombined as a single nucleic acid which is then recombined with the target locus.

The method of the invention may be carried out where recombination of the said two or more nucleic acids with each other and with the target locus takes place simultaneously.

In a method of the invention two of the at least two nucleic acids may each comprise a part of the recombinase-encoding sequence such that together they comprise the entire recombinase-encoding sequence.

The method of the invention may be carried out so that the recombinase directed against the site-specific recombination sites is expressed such that the sequence located between the two site-specific recombination sites is out-recombined.

The expression of the recombinase will typically be under the control of a promoter which enables expression of the recombinase within the host cell. That is to say, the recombinase encoding sequence will typically be in operable linkage with a promoter sequence. The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter. Expression of the recombinase by an inducible promoter will allow out-recombination of the sequence located between the site-specific recombination sites to be controlled, for example including the recombinase encoding sequence.

Examples of inducible promoters that can be used are a starch-, cellulose-, hemicellulose (such as xylan- and/or xylose-inducible), copper-, oleic acid-inducible promoters. The promoter may be selected from the group, which includes but is not limited to promoters obtained from the polynucleotides encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933.

As set out herein, in a method of the invention, the two or more nucleic acids, taken together, may comprise a sequence encoding a marker so that recombination of the two or more nucleic acids results in the said marker-encoding sequence being located between the homologous recombination sites.

Recombination of the two or more nucleic acids may result in the said marker-encoding sequence being located between the site-specific recombination sites such that the marker may be out-recombined on expression of the recombinase.

Any suitable marker may be used and such markers are well-known to determine whether a nucleic acid is included in a cell. Typically, a marker, such as a selectable marker, permits easy selection of transformed cells. A selectable marker is a gene the product of which provides for biocide or viral resistance, resistance to heavy metals, prototrophy to auxotrophs, and the like.

Examples of marker genes include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotic resistance markers (e.g., β-lactamase), β-galactosidase, fluorescent or other coloured markers, such as green fluorescent protein (GFP), yellow fluorescent protein (YFP), red fluorescent protein (RFP) and cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments as described in 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), as well as equivalents from other species. Preferred for use in an Aspergillus and Penicillium cell are the amdS (see for example EP 635574 B1, EP0758020A2, EP1799821A2, WO 97/06261A2) and pyrG genes of A. nidulans or A. oryzae and the bar gene of Streptomyces hygroscopicus. More preferably an amdS gene is used, even more preferably an amdS gene from A. nidulans or A. niger. A most preferred selectable marker gene is the A. nidulans amdS coding sequence fused to the A. nidulans gpdA promoter (see EP 635574 B1). Other preferred AmdS markers are those described in WO2006/040358. AmdS genes from other filamentous fungi may also be used (WO 97/06261).

In the method of the invention, the in vivo recombination may be carried out in any suitable host cell, for example carried out in a prokaryotic or a eukaryotic cell. A suitable eukaryotic host cell may be a mammalian, insect, plant, fungal or algal cell. A host cell may be a microorganism or microbial host cell, for example a prokaryotic or eukaryotic host cell. Typically, the method of the invention will not be carried out in vivo in a human or animal.

Typically, a host cell used in the method according to the invention may be one suitable for the production of a compound of interest and the selection of the host cell may be made according to such use. For example, if the compound of interest produced in a host cell according to the invention is to be used in food applications, a host cell may be selected from a food-grade organism such as Saccharomyces cerevisiae. Specific uses include, but are not limited to, food, (animal) feed, pharmaceutical, agricultural such as crop-protection, and/or personal care applications.

The method of the invention may be used to confer on a host cell the ability to produce the compound of interest and/or to modify the way in which an existing compound of interest is produced, for example to increase the production of such a compound of interest.

A microbial host cell suitable for use in the method according to the invention may be a prokaryotic cell. Preferably, the prokaryotic host cell is a bacterial cell. The term "bacterial cell" includes both Gram-negative and Gram-positive microorganisms. Suitable bacteria may be selected from e.g. Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus or Streptomyces. Preferably, the bacterial cell is selected from the group consisting of B. subtilis, B. amyloliquefaciens, B. licheniformis, B. puntis, B. megaterium, B. halodurans, B. pumilus, G. oxydans, Caulobactert crescentus CB 15, Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti and Rhizobium radiobacter.

A host cell suitable for use in the invention may be a eukaryotic host cell. Such a eukaryotic cell may be a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, for example a yeast cell, such as Candida, Hansenula, Kluyveromyces, Pichia, Saccharomyces, Schizosaccharomyces, or Yarrowia strain. More preferably from Kluyveromyces lactis, S. cerevisiae, Hansenula polymorpha, Yarrowia lipolytica and Pichia pastoris. Most preferably, the eukaryotic cell is a filamentous fungal cell.

Filamentous fungi include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium, and Trichoderma.

Preferred filamentous fungal cells belong to a species of an Acremonium, Aspergillus, Chrysosporium, Myceliophthora, *Penicillium, Talaromyces, Thielavia, Fusarium* or *Trichoderma* genus, and most preferably a species of *Aspergillus niger, Acremonium alabamense, Aspergillus awamori, Aspergillus foetidus, Aspergillus sojae, Aspergillus fumigatus, Talaromyces emersonii, Aspergillus oryzae, Chrysosporium lucknowense, Fusarium oxysporum, Myceliophthora thermophila, Trichoderma reesei, Thielavia terrestris* or *Penicillium chrysogenum*. A more preferred host cell belongs to the genus *Aspergillus*, more preferably the host cell belongs to the species *Aspergillus niger*. When the host cell according to the invention is an *Aspergillus niger* host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present invention may be *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin54-1255 (ATCC28089), *Penicillium citrinum* ATCC 38065, *Penicillium chrysogenum* P2, *Thielavia terrestris* NRRL8126, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof.

Preferably the microbial host cell according to the invention which has been modified in its genome such that it results in a deficiency in the production of at least one non-ribosomal peptide synthase has not been modified to disrupt the gliP gene encoding for a non-ribosomal peptide synthase responsible for gliotoxin production. Preferably the microbial host cell according to the invention which has been modified in its genome such that it results in a deficiency in the production of at least one non-ribosomal peptide synthase is not an *Asperigllus fumigatus* host cell which has been modified to disrupt the gliP gene encoding for a non-ribosomal peptide synthase responsible for gliotoxin production.

Preferably, when the host cell used in the methods according to the invention is a filamentous fungal host cell, the host cell which has been modified in its genome such that it results in a deficiency in the production of at least one non-ribosomal peptide synthase, preferably a non-ribosomal peptide synthase according to the invention, more preferably a non-ribosomal peptide synthase npsE (see WO2012/001169) additionally comprises one or more modifications in its genome in a polynucleotide encoding a product selected from the group of glucoamylase (glaA), acid stable alpha-amylase (amyA), neutral alpha-amylase (amyBI and amyBII), oxalic acid hydrolase (oahA), a toxin, preferably ochratoxin and/or fumonisin, and protease transcriptional regulator prtT such that the host cell is deficient in at least one product encoded by the polynucleotide comprising the modification.

Therefore the fungal host cell additionally comprises modifications in its genome such that it is deficient in at least one of glucoamylase (glaA), acid stable alpha-amylase (amyA), neutral alpha-amylase (amyBI and amyBII), oxalic acid hydrolase (oahA), a toxin, such as ochratoxin and fumonisin, preferably ochratoxin and/or fumonisin, more preferably ochratoxin A and/or fumonisin B2, and protease transcriptional regulator prtT. Preferably, the host cell additionally comprises one or more modifications in its genome in a polynucleotide encoding the major extracellular aspartic protease PepA such that the host cell is deficient in the major aspartic protease PepA. For example the host cell according to the invention may further comprise a disruption of the pepA gene encoding the major extracellular aspartic protease PepA. Preferably the host cell according to the invention additionally comprises one or more modifications in its genome in a polynucleotide encoding the hdfA gene such that the host cell is deficient in hdfA. For example the host cell according to the invention may further comprise a disruption of the hdfA gene.

Preferably the host cell additionally may comprise at least two substantially homologous DNA domains suitable for integration of one or more copies of a polynucleotide encoding a compound of interest wherein at least one of the at least two substantially homologous DNA domains is adapted to have enhanced integration preference for the polynucleotide encoding a compound of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains. These cells have been described in WO2011/009700. Strains containing two or more copies of these substantially homologous DNA domains are also referred hereafter as strain containing two or more amplicons. Examples of host cells comprising such amplicons are e.g. described in van Dijck et al, 2003, Regulatory Toxicology and Pharmacology 28; 27-35: *On the safety of a new generation of DSM Aspergillus niger enzyme production strains*. In van Dijck et al, an *Aspergillus niger* strain is described that comprises 7 amplified glucoamylase gene loci, i.e. 7 amplicons. In this context preferred host cells which may contain two or more amplicons belong to a species of an *Acremonium, Aspergillus, Chrysosporium, Myceliophthora, Penicillium, Talaromyces, Thielavia, Fusarium* or *Trichoderma* genus, and more preferably a species of *Aspergillus niger, Acremonium alabamense, Aspergillus awamori, Aspergillus foetidus, Aspergillus sojae, Aspergillus fumigatus, Talaromyces emersonii, Aspergillus oryzae, Chrysosporium lucknowense, Fusarium oxysporum, Myceliophthora thermophila, Trichoderma reesei, Thielavia terrestris* or *Penicillium chrysogenum*.

Preferred host cells within this context are filamentous fungus host cells, preferably *A. niger* host cells, comprising two or more amplicons, preferably two or more ΔglaA amplicons (preferably comprising 3, 4, 5, 6, 7 ΔglaA amplicons) wherein the amplicon which has the highest frequency of gene conversion, has been adapted to have enhanced integration preference for the polynucleotide encoding a compound of interest compared to the amplicon it originates from. Adaptation of the amplicon can be performed according to any one of the methods described in WO2011/009700 (which is here fully incorporated by reference). An example of these host cells, described in WO2011/009700, are host cells comprising three ΔglaA amplicons being a BamHI truncated amplicon, a SalI truncated amplicon and a BglII truncated amplicon and wherein the BamHI amplicon has been adapted to have enhanced integration preference for a polynucleotide encoding a compound of interest compared to the BamHI amplicon it originates from. Host cells comprising two or more amplicons wherein one amplicon has been adapted to have enhanced integration preference for a polynucleotide encoding a compound of interest compared to the amplicon it originates from are hereafter referred as host cells comprising an adapted amplicon.

Preferably, the host cell according to the invention additionally comprises a modification of Sec61. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. Most preferably, the SEC 61 modification is the S376W mutation in which Serine 376 is replaced by Tryptophan.

A preferred filamentous fungal host cell used in the method according to the invention, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII) and oxalic acid hydrolase (oahA). Another preferred host cell, deficient in a non-ribosomal peptide synthase, preferably a non-ribosomal peptide synthase as defined above additionally is deficient in pepA, glucoamylase (glaA), acid stable alpha-amylase (amyA), neutral alpha-amylase (amyBI and amyBII), oxalic acid hydrolase (oahA) and hdfA. Another preferred host cell, deficient in a non-ribosomal peptide synthase, preferably a non-ribosomal peptide synthase as defined above additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin and hdfA. Another preferred host cell, deficient in a non-ribosomal peptide synthase preferably a non-ribosomal peptide synthase as defined above, additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin and hdfA. Preferably, these host cells are also deficient in prtT. Therefore another preferred host cell, deficient in a non-ribosomal peptide synthase, preferably a non-ribosomal peptide synthase as defined above, additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin, prtT and hdfA.

Another preferred host cells, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), ochratoxin, fumonisin, prtT, hdfA and comprises a SEC 61 modification being a S376W mutation in which Serine 376 is replaced by Tryptophan.

Preferably these host cells are filamentous fungal cells, more preferably A niger host cells comprising an adapted amplicon as defined above. Therefore the host cells used in the method according to the invention, deficient in a non-ribosomal peptide synthase, preferably deficient in a non-ribosomal peptide synthase according to the invention, more preferably in a non-ribosomal peptide synthase npsE (see WO2012/001169) are filamentous fungus host cells, preferably A. niger host cells additionally deficient in pepA, glucoamylase (glaA), acid stable alpha-amylase (amyA), neutral alpha-amylase (amyBI and amyBII) and oxalic acid hydrolase (oahA) and comprising an adapted amplicon as defined above. Another preferred filamentous fungus host cell such as an A. niger host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA) and hdfA and comprises an adapted amplicon as defined above. Another preferred filamentous fungus host cell such as an A. niger host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin and hdfA and comprises an adapted amplicon as defined above. Another preferred filamentous fungus host cell such as an A. niger host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin and hdfA and comprises an adapted amplicon as defined above. Another preferred filamentous fungus host cell such as an A. niger host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin prtT and hdfA and comprises an adapted amplicon as defined above.

Another preferred filamentous fungus host cell such as an A. niger host cells, deficient in a non-ribosomal peptide synthase preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin, prtT, hdfA, comprises a SEC 61 modification being a S376W mutation in which Serine 376 is replaced by Tryptophan and comprises an adapted amplicon as defined above.

Typically, in the invention, the host cell will be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

The compound of interest may a primary metabolite, secondary metabolite, a peptide or polypeptide or it may include biomass comprising the host cell itself. The compounds of interest may be an organic compound selected from glucaric acid, gluconic acid, glutaric acid, adipic acid, succinic acid, tartaric acid, oxalic acid, acetic acid, lactic acid, formic acid, malic acid, maleic acid, malonic acid, citric acid, fumaric acid, itaconic acid, levulinic acid, xylonic acid, aconitic acid, ascorbic acid, kojic acid, comeric acid, an amino acid, a poly unsaturated fatty acid, ethanol, 1,3-propane-diol, ethylene, glycerol, xylitol, carotene, astaxanthin, lycopene and lutein. Alternatively, the fermentation product may be a β-lactam antibiotic such as Penicillin G or Penicillin V and fermentative derivatives thereof, a cephalosporin, cyclosporin or lovastatin.

The compound of interest may be a peptide selected from an oligopeptide, a polypeptide, a (pharmaceutical or industrial) protein and an enzyme. In such processes the peptide is preferably secreted from the host cell, more preferably secreted into the culture medium such that the peptide may easily be recovered by separation of the host cellular biomass and culture medium comprising the peptide, e.g. by centrifugation or (ultra)filtration.

Examples of proteins or (poly)peptides with industrial applications that may be produced in the methods of the invention include enzymes such as e.g. lipases (e.g. used in the detergent industry), proteases (used inter alia in the detergent industry, in brewing and the like), carbohydrases and cell wall degrading enzymes (such as, amylases, glucosidases, cellulases, pectinases, beta-1,3/4- and beta-1,6-glucanases, rhamnoga-lacturonases, mannanases, xylanases, pullulanases, galactanases, esterases and the like, used in fruit processing, wine making and the like or in feed), phytases, phospholipases, glycosidases (such as amylases, beta.-glucosidases, arabinofuranosidases, rhamnosidases, apiosidases and the like), dairy enzymes and products (e.g. chymosin, casein), polypeptides (e.g. poly-lysine and the like, cyanophycin and its derivatives). Mammalian, and preferably human, polypeptides with therapeutic, cosmetic or diagnostic applications include, but are not limited to, collagen and gelatin, insulin, serum albumin (HSA), lactoferrin and immunoglobulins, including fragments thereof. The polypeptide may be an antibody or a part thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase.

For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: *The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. For purpose of the invention, the parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The protein sequences mentioned herein can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences and BLASTN for nucleotide sequences. In the BLAST program, the default settings may be used:

Cost to open gap: default=5 for nucleotides/11 for proteins
Cost to extend gap: default=2 for nucleotides/1 for proteins
Penalty for nucleotide mismatch: default=−3
Reward for nucleotide match: default=1
Expect value: default=10
Wordsize: default=11 for nucleotides/28 for megablast/3 for proteins The nucleic acid sequences as mentioned herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, word-length=12 to obtain nucleotide sequences homologous to the nucleic acid molecules of the invention.

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a nucleic acid sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1. A Method for Efficient Integration and Out-Recombination of a Marker Using a "Split Cre/Lox" Approach 1.1 General Principle of Split Cre Recombinase Integration The original method using Cre/loxP, described by Gueldener et al (1996), consists of a three step process. Step one is transformation of the marker surrounded by two loxP sites integrating it in the genome, which may result for example in the deletion of a gene. Step two is transformation of a plasmid containing the Cre recombinase under control of the GAL1 galactose inducible promoter. After induction of the Cre recombinase with galactose and removal of the marker via recombination of the loxP sites, the third step consists of removal of the plasmid which is often less straightforward than expected. The method described in this example, "split Cre recombinase integration" or "direct Cre recombinase integration" (DCI), is more efficient and much faster. This approach for genomic integration and removal of a selection marker takes less effort and only one transformation step.

FIG. 1 shows a schematic drawing of the deletion of ICL1 using the DCI method. Use of the DCI method requires only one transformation of the strain from which a gene is to be deleted and no plasmid need be removed from the strain. In addition, all fragments used can easily be prepared by PCR amplification, in this Example 4 fragments are used. The open reading frame of the Cre recombinase gene is split into two parts, so as to prevent all activity of the recombinase until all four PCR fragments recombine on the genome as shown in FIG. 1. After recombination, marker and Cre recombinase are flanked by loxP sites (in this case lox66 and lox71 [Albert, H., Dale, E. C., Lee, E., & Ow, D. W. (1995). Site-specific integration of DNA into wild-type and mutant lox sites placed in the plant genome. Plant Journal, 7(4), 649-659]) and induction of the Cre recombinase causes the marker including the Cre recombinase to be excised from the genome via the recombination at the lox66 and lox71 sites. Splitting up the Cre recombinase is an important feature of the method since it prevents unwanted activity of the Cre recombinase in the E. coli strain carrying the plasmids with loxP sites. Such activity would easily cause instability in any plasmid harbouring loxP sites and Cre recombinase. The experimental procedures and methods used for the DCI method will be further explained in this Example.

1.2 Synthesis and Cloning of the Split Cre/loxP Fragments Cre-1 and Cre-2

Figure 2:
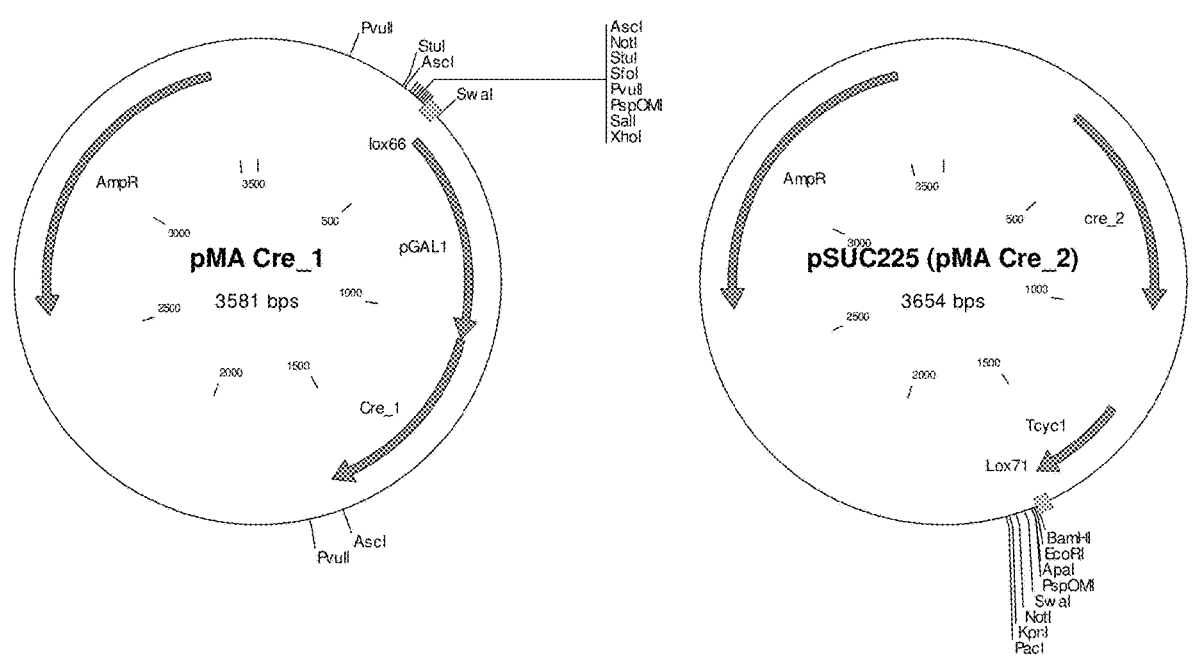
FIG. 2 sets out plasmid maps of pMA Cre-1 and pMA Cre-2 (pSUC225). pMA Cre-1 contains the lox66 site, GAL1 promoter and the inactive 5' part of the Cre recombinase open reading frame and pSUC225 contains the 3' inactive part of the Cre recombinase open reading frame the CYC1 terminator and the lox71 site.

The two split Cre/loxP fragments, Cre-1 and Cre-2 (SEQ ID Nos: 1 and 2), were synthesized by Geneart (Regensburg, Germany). Fragment Cre-1 carries, from upstream to downstream: the lox66 recombination site; a SwaI site to clone in selection markers; the inducible GAL1 promoter; and the 5' part of the Cre recombinase open reading frame. Fragment Cre-2 carries, from upstream to downstream: the 3' part of the Cre recombinase having a 100 bp overlap with the Cre-1 fragment; the CYC1 terminator; and the lox71 site for recombination. Upstream of the lox66 site and downstream of the lox71 site, several unique restriction sites were added in order to create the possibility of cloning in expression cassettes. It is also possible to use in vivo homologous recombination to add expression cassettes, by adding a 50 bp overlap between each following expression cassette. Upon integration of the Cre-1 and Cre-2 fragments into a genome, the Cre recombinase open reading frame is restored to a functional open reading frame via in vivo homologous recombination of the 100 bp overlap. After synthesis, Geneart cloned both of the Cre-1 and Cre-2 fragments into the pMA vector creating the constructs pMA Cre-1 (SEQ ID No: 3) and pMA Cre-2 (SEQ ID No: 4) for which the plasmid maps are shown in FIG. 2. The plasmid pMA Cre_2 was renamed pSUC225. The next step was the cloning of a functional marker into the multiple cloning site of pMA Cre-1.

1.3 Cloning of the kanMX Marker into the pMA Cre-1 Vector

Figure 3:
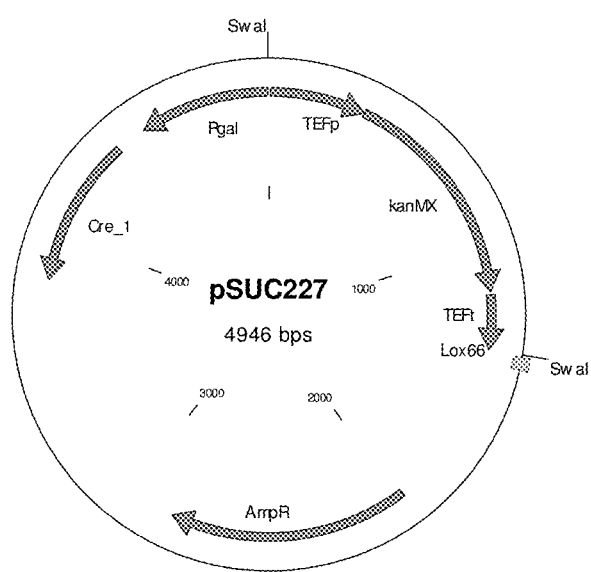
FIG. 3 sets out the plasmid map of pSUC227. The plasmid contains the lox66 site, the kanMX marker cassette, the GAL1 promoter and the inactive 5' part of the Cre recombinase open reading frame.

The kanMX marker, conferring resistance to G418, was amplified from a pUG6 derived plasmid (SEQ ID No: 5) with the primers DBC-02738 and DBC-02739 (SEQ ID Nos: 6 and 7). The original pUG6 can be used in the PCR reaction as well, pUG6 plasmid was obtained from EURO-SCARF (Güldener et al, 1996) PCR reaction was performed with Phusion polymerase (Finnzymes, Vantaa, Finland) according to the manual. The primers used added a SwaI restriction site on both sides of the kanMX marker, making it possible to clone the marker into the pMA Cre-1 vector. The obtained PCR fragment of 1381 bp was cloned into the "pCR-Blunt II-TOPO" vector with the "Zero Blunt TOPO PCR Cloning" Kit from Invitrogen (Carlsbad, USA). All steps were performed according to the protocol supplied by Invitrogen. The resulting clones were checked with SwaI digestion followed by analysis on an agarose electrophoresis gel to confirm insert size. The resulting pCR-Blunt II-TOPO vector with kanMX marker (SEQ ID No: 8) was cut with SwaI to isolate the kanMX marker fragment. The SwaI digested kanMX marker was ligated into the SwaI digested pMA Cre-1 vector and the resulting clones were checked with HindIII. Multiple clones showed the correct fragment size of 3541 bp and 1405 bp on gel and one of the clones was stored and named pSUC227 (SEQ ID No: 9). FIG. 3 shows the plasmid map of pSUC227.

1.4 Preparation and Purification of PCR Fragments for Transformation

All 4 fragments necessary for transformation and deletion of ICL1 in CEN.PK113-7D were prepared with PCR. Each PCR fragment has homology to the neighbouring fragment enabling the in vivo homologous recombination system of *S. cerevisiae* to recombine and integrate the four fragments at the locus of the ICL1 gene. The 5' flanking fragment upstream of the ICL1 gene (629 bp, SEQ ID No: 10) was amplified with primer pair DBC-03754(SEQ ID No: 11) and DBC-03755 (SEQ ID No: 12). The 3' flanking fragment downstream of the ICL1 gene (603 bp, SEQ ID No: 13) was amplified with primer pair DBC-03758 (SEQ ID No:14) and DBC-03759 (SEQ ID No: 15). Both flanks were PCR amplified with chromosomal DNA isolated from CEN.PK113-7D as template DNA. The "Cre-1-kanMX" fragment (2586 bp, SEQ ID No: 16) was amplified with primer pair DBC-03756 (SEQ ID No: 17) and DBC-03373 (SEQ ID No: 18) using pSUC227 as template. The Cre-2 fragment (1274 bp, SEQ ID No: 19) was amplified with primer pair DBC-03374 (SEQ ID No: 20) and DBC-03757 (SEQ ID No: 21) using pSUC225 as template. All PCR reactions were performed with Phusion polymerase (Finnzymes) according to the manual. The size of the PCR fragments was checked with standard agarose electrophoresis techniques. PCR amplified DNA fragments were purified with the DNA purification kit "Clean and Concentrator" from Zymo Research (Irvine, USA), according to the manual. The DNA concentration was measured using A260/A280 on a Nanodrop ND-1000 spectrophotometer.

1.5 Transformation to *S. cerevisiae* and Deletion of ICL1 with Split Cre-Lox

Transformation of *S. cerevisiae* was carried out as described by Gietz and Woods (2002; Transformation of the yeast by the LiAc/SS carrier DNA/PEG method. Methods in Enzymology 350: 87-96). CEN.PK113-7D (MATa URA3 HIS5 LEU2 TRP1 MAL2-8 SUC2) was transformed with the following amounts of purified PCR fragments:1 μg of fragment "Cre-1-kanMX"; 1 μg of fragment Cre-2; 0.8 μg of the 5' flanking fragment upstream of the ICL1 gene; and 0.5 μg of the 3' flanking fragment downstream of the ICL1 gene. Transformation mixtures were plated on YEP agar (Peptone 10.0 g/I, Yeast Extract 10.0 g/I, Sodium Chloride 5.0 g/I, Agar 15.0 g/1) with 20 g/I dextrose and 200 μg/ml G418 (Sigma). After 3-5 days incubation at 30° C., plates were checked and approximately 230 colonies appeared on the plates, whereas the negative control (i.e. no addition of DNA in the transformation experiment) resulted in blank plates.

1.6 Efficient Out-Recombination of the Marker Cassette and Cre Recombinase

Six colonies were picked from the plates and restreaked on YEP agar plates with 2% galactose for induction of the Cre recombinase. Plates were incubated for 2 days at 30° C. During this incubation the galactose induced Cre recombinase mediates the efficient out-recombination of marker and Cre recombinase. Two single colonies from each restreaked transformant, in total 12 isolates, were transferred with an inoculation loop to a fresh plate of YEP agar with 2% galactose for storage. In addition, the same colonies were transferred with an inoculation loop to 2 ml YEP medium (Peptone 10.0 g/I, Yeast Extract 10.0 g/I, Sodium Chloride 5.0 g/1) with 20 g/I galactose in a 12 ml greiner tube. After 0/N incubation at 30° C. and 280 rpm on a rotary shaker, 1.5 ml of these cultures was transferred to an Eppendorf tube and centrifuged for 1 minute at maximum speed. From this cell pellet, chromosomal DNA was isolated for further PCR and sequencing analysis (as described in section 1.7 below).

1.7 Analysis Confirming the Deletion of ICL1 and Absence of Marker and Cre

Figure 4:
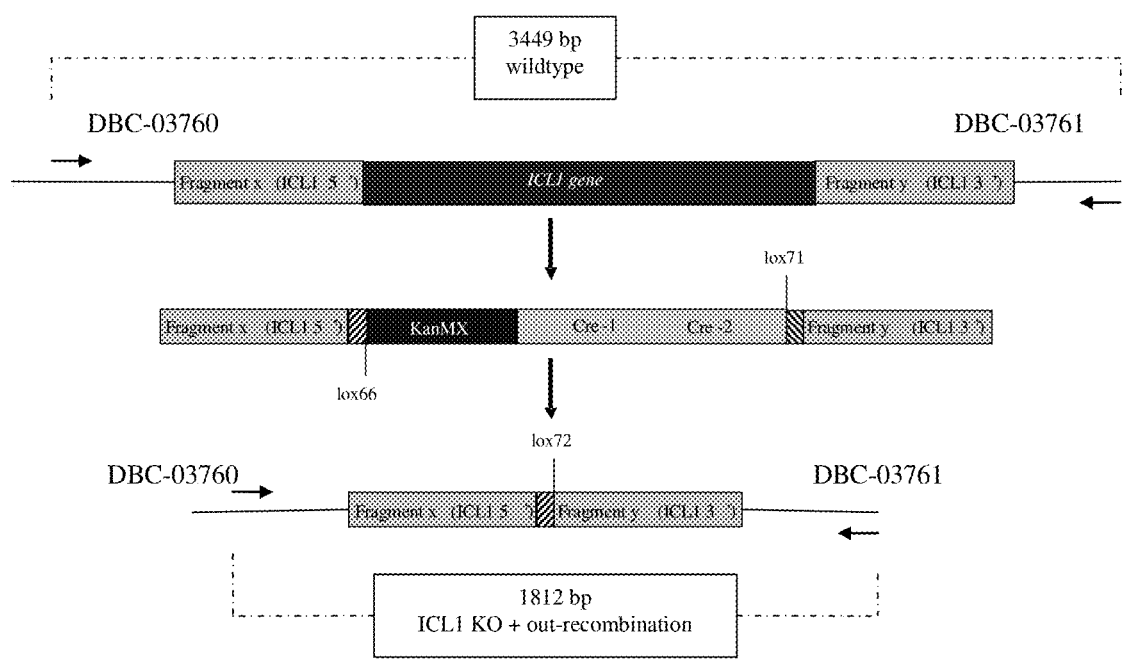
FIG. 4 sets out PCR reactions with primer pair DBC-03670 and DBC-03761 amplifying the genomic locus of the ICL1 gene, resulting in a 3449 bp PCR fragment in the wild-type situation and a 1812 bp PCR fragment in the KO situation with marker removed by recombination of lox66 and lox71.

Chromosomal DNA was isolated from the cell pellets using the DNeasy Blood & Tissue kit from QIAGEN with an adapted protocol using R-zymolyase. The primer combination DBC-03760 (SEQ ID No: 22) and DBC-03761 (SEQ ID No: 23) was used for PCR analysis. In the wild type situation, a band of 3449 bp (SEQ ID No: 24) is expected. When the ICL1 marker and Cre recombinase are lost, the PCR will result in a band of 1812 bp (SEQ ID No: 25). FIG. 4 shows the situation on the genome and the location of the primers used. PCR reactions were performed with Phusion polymerase (Finnzymes) according to the manual. The size of the PCR fragments was checked with standard agarose electrophoresis techniques. All colonies tested showed the specific band of 1.8 kb which is the correct size for deletion of ICL1 and out-recombination of the kanMX marker and Cre recombinase. The PCR fragments were sent to Baseclear (Leiden, Netherlands) for sequencing and the sequencing results confirmed the conclusions from the PCR analysis. The resulting sequence obtained from Baseclear was an exact match with sequence identity 25 and showed that the ICL1 gene has been deleted from the genome and that efficient out-recombination of the kanMX marker and Cre recombinase had taken place leaving the lox72 site as a result of recombination between the lox66 and lox71 sites.

The experiments in the Example demonstrate that the "split Cre/lox" approach is a fast, robust technique for generating reusable, markerless *S. cerevisiae* strains.

Example 2

2.1 Synthesis and Preparation of the Split Cre/loxP Fragments 5'Split CRE and 3'Split CRE A candidate for disruption (epo gene) was identified in the genome sequence of *A. niger* CBS513.88. All nucleotide sequences for *A. niger* genes and their genomic context can be derived for example from NCBI (http://www.ncbi.nlm.nih.gov/) of EMBL (http://www.ebi.ac.uk/embl/). The epo gene is encoded by An08g04490. The strain *Aspergillus niger* GBA 302 (ΔglaA, ΔpepA, ΔhdfA) is used herein as recipient strain in transformations. Construction of GBA 302 is described in WO2011009700.

Gene replacement vectors were designed according to known principles and constructed according to routine cloning procedures as also described in EP635574B and WO 98/46772. In essence, these vectors comprise approximately 1-2 kb flanking regions of the respective ORF sequences, to target for homologous recombination at the predestined genomic loci. They may contain for example the *A. nidulans* bi-directional amdS selection marker, the hygromycin B marker or the phleomycin selection marker for transformation. The method applied for gene replacements in all examples herein uses linear DNA, which integrates into the genome at the homologous locus of the flanking sequences by a double cross-over, thus substituting the gene to be deleted by a marker gene (such as the amdS gene). Loss of the amdS marker for example can be selected for by plating on fluoro-acetamide media.

Two different deletion vectors pEPO-US and pEPO-DS were designed to be able to provide two overlapping DNA molecules for split cre/loxP gene-targeting. The insert fragments in both vectors together can be applied as replacement cassette in a fashion somewhat similar to the so-called "bipartite gene-targeting" method (Nielsen et al., 2006, 43: 54-64). This method described by Nielsen is using two DNA fragments, which are overlapping in sequence (see also WO2008113847 for further details of the bipartite method), and both with a non-functional selection marker together with gene-targeting sequences at their flankings. Upon correct homologous recombination of the overlapping non-functional marker fragments, the selection marker becomes functional by integration at a homologous target locus.

Figure 5:
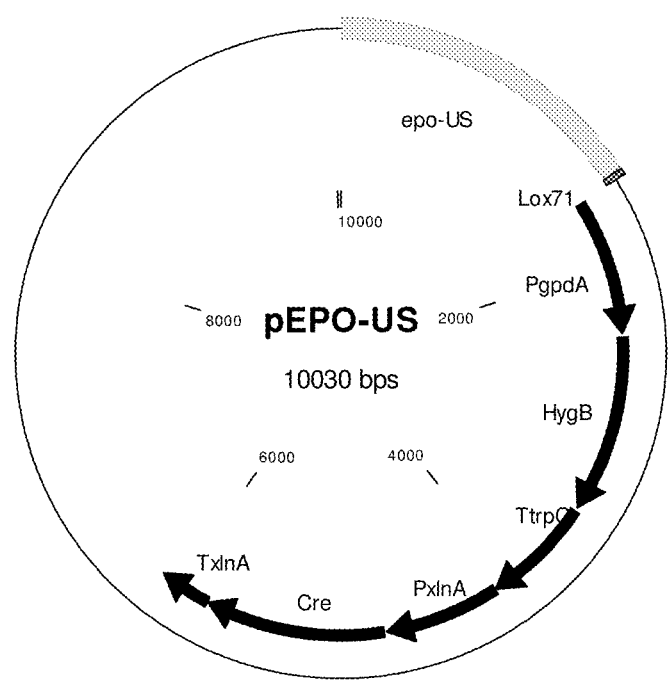
FIG. 5 sets out a schematic representation of plasmid pEPO-US, which comprises part of a replacement cassette used to inactivate the epo gene in *A. niger* and *E. coli* plasmid DNA. The replacement cassette comprises an epo flanking region for targetting, a mutant loxP site, a functional hygB marker cassette and an inducible cre recombinase expression cassette. More details for pEPO-US can be found in the Examples section (vide infra).
Figure 6:
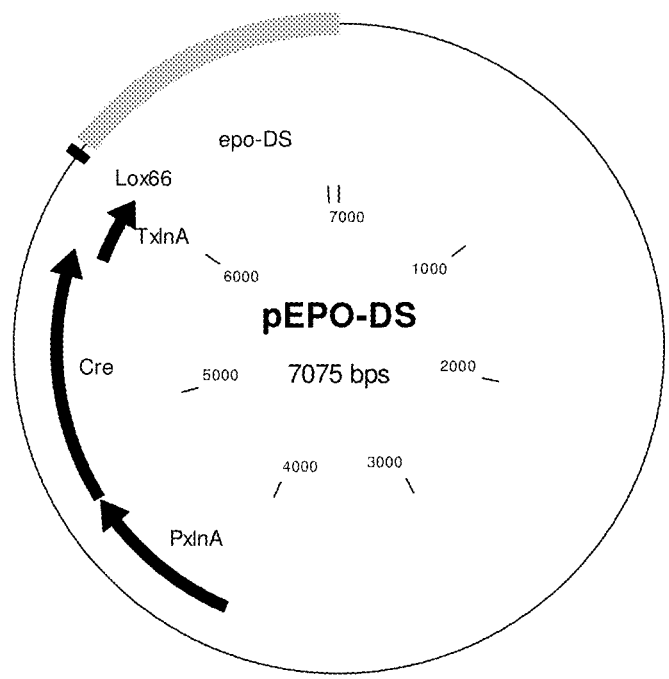
FIG. 6 sets out a schematic representation of plasmid EPO-DS, which comprises part of a replacement cassette used to inactivate the epo gene in *A. niger* and *E. coli* plasmid DNA. The replacement cassette comprises an epo flanking region for targetting, a cre recombinase expression cassette, a mutant loxP site. More details for EPO-DS can be found in the Examples section (vide infra).
Figure 7:
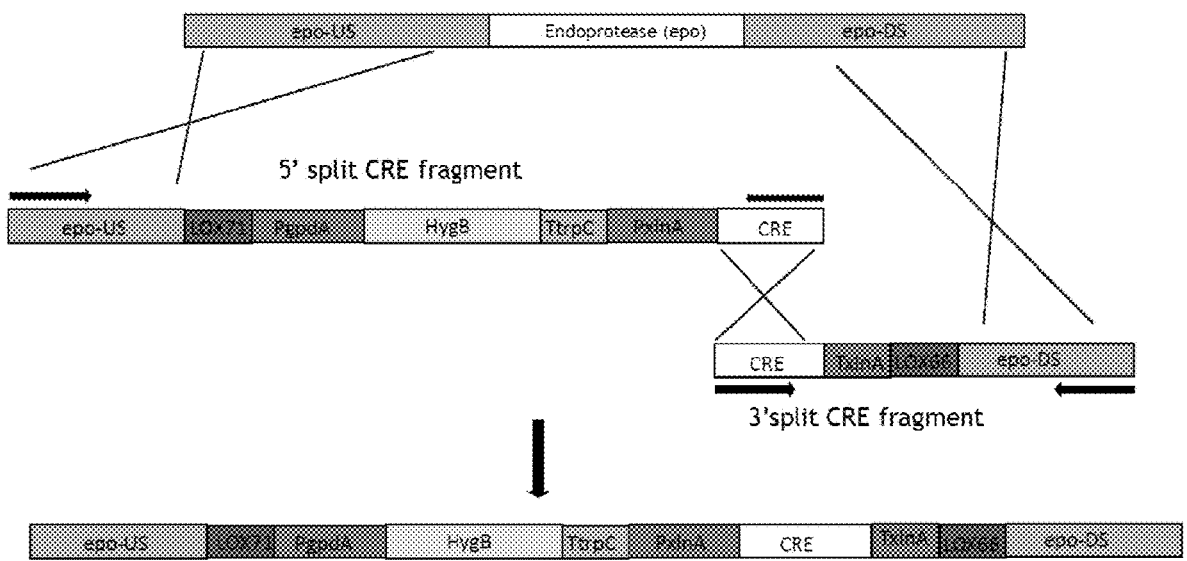
FIG. 7 sets out a schematic representation for fragment generation of a 5' split CRE fragment and a 3' split CRE fragment and a possible layout how to use of these overlapping fragments in transformation and targeted recombination in *A. niger*. The top panel indicates the genomic DNA composition of the gene to be targeted. In the middle panel the generation of the "5' split CRE" and "3' split CRE" fragments as amplified by PCR is demonstrated. In the lower panels, *A. niger* transformation through homologous recombination of the 5' split CRE and 3' split CRE within the genome is shown.

The first vector pEPO-US (General layout of functional fragments as in FIG. 5) comprises a functional hygB marker fragment (PgpdA-HygB-TtrpC from pAN7-1, NCBI gi: 475166), a Lox71 sequence site, a cre recombinase cassette and a 5'-upstream gene flanking region (e.g. promoter region) of the epo ORF (epo-US). The cre recombinase cassette used herein contains the *A. nidulans* xylanase A promoter, a cre recombinase and xylanase A terminator, to allow xylose-inducible expression of the cre recombinase. The second pEPO-DS vector (General layout of functional fragments as in FIG. 6) comprises a cre recombinase cassette, a Lox66 sequence site and a 3'-downstream gene flanking region of the epo ORF (epo-DS). Both epo upstream and downstream gene flanking regions target for homologous recombination of the bipartite fragments at the predestined epo genomic locus in *A. niger*.

In the following example we show that the split cre system as used herein is a very efficient system for gene disruption when using strains deficient in NHEJ.

2.2 Efficient Gene Deletion Using Split Cre/loxP Overlapping DNA Fragments

Use of a mutant which is deficient in a gene encoding a component involved in NHEJ, such as inactivation of at least one of the hdfA, hdfB, lig4, etc. . . . genes results in a significant increase of the targeting efficiency observed for integration vectors through (double) homologous recombination (as earlier described in WO2005095624 and WO2008113847 for example).

In addition, increase of the targeting efficiency for homologous recombination can be obtained as described in WO2008113847. This bipartite gene-targeting method described therein, comprises providing two sets of DNA molecules of which the first set comprises DNA molecules each comprising a first non-functional fragment of the replacement sequence of interest flanked at its 5'-side by a DNA sequence substantially homologous to a sequence of the chromosomal DNA flanking the target sequence and the second set comprises DNA molecules each comprising a second non-functional fragment of the DNA replacement sequence of interest overlapping with the first non-functional fragment and flanked at its 3'-side by a DNA sequence substantially homologous to a sequence of the chromosomal DNA flanking the target sequence, wherein the first and second non-functional fragments become functional upon recombination.

Gene replacement vectors pEPO-US and pEPO-DS (layouts as described in Example 2.1) both comprise approximately a 1 kb flanking region for homologous recombination at the target epo ORF. In addition, they both contain the bacteriophage P1 Cre gene under control of the *A. nidulans* xylanase A promoter to allow inducible Cre expression upon xylose induction and a loxP site (lox71 or lox66).

The pEPO-US construct also contains a functional and full length hygB selection marker cassette.

In a method according the invention, two linear split cre gene-targeting fragments for epo disruption are generated by PCR in sufficient quantities using the pEPO-US and pEPO-DS plasmids as template (SEQ ID Nos: 26-31). The overlap of the two nucleotide fragments at the cre gene is around 1 kb in this case. It is anticipated that the two fragments overlapping at the cre gene can contain a non-functional and/or partial gene as well as a functional and/or full length cre gene. For each fragment, 1.5 µg of DNA is used to transform *Aspergillus niger* GBA302. Transformants are selected based on hygromycin B resistance, colony purified according to standard procedures as described in EP635574B and subsequently analyzed after purification. Based on transformations using the two different overlapping PCR fragments generated on pEPO-US and pEPO-DS, hygromycin resistant colonies will be identified. After analysis of the hygromycin-resistant transformants, over 90% of the transformants will show a proper and targeted integration at the epo target locus. It is anticipated that genomic DNA of transformants having a correct integration of the targeting disruption cassette at the epo locus comprising the mutant loxP sites, the hygromycin resistance cassette and the inducible Cre recombinase cassette, can be used as template DNA in PCR for example for amplification of bipartite and/or full disruption DNA fragments to be used in construction of host strains.

For inducing the cre-recombinase under control of the xylanase promoter, minimal medium agar plates containing 1% xylose and 1% glucose (xylanase inducing medium) are used. When Cre recombinase is induced by xylose, deletion of the DNA cassette in between the two specific loxP sites can occur by excision. Resulting colonies after growth on xylanase inducing medium with optionally additional sporulation and purification steps are tested for their hygromycin B resistance. These spores from the transformants after xylose induction and optionally addition purification steps are transferred to PDA plates with and without hygromycin B (60 µg/ml) using toothpicks. Loss of hygromycin B resistance likely is coupled to loss of the hygB marker cassette through cre recombinase activity. It can be anticipated that the majority of the colonies tested after growth and sporulation on xylanase induction medium and two additional purification steps is sensitive to hygromycin and has lost both the hygB cassette and cre recombinase gene simultaneously This Example shows that in a fungal strain deficient in NHEJ, use of split cre/loxP DNA fragments for gene-targeting is highly efficient. The use of split cre/loxP DNA fragments in combination with an inducible Cre recombination system according the invention allows for a very efficient strain construction/disruption in building marker-free strains without the need of a second transformation or counter-selection procedures in strain construction.

The invention claimed is:

1. A method for carrying out recombination at a target locus in a host cell, which method comprises:
    providing two or more nucleic acids which comprise: (a) sequences capable of homologous recombination with sequences flanking the target locus; (b) two or more site-specific recombination sites; and (c) a sequence encoding a recombinase which recognizes the site-specific recombination sites,
    wherein none of the two or more nucleic acids comprises all of the sequences of (a), (b), and (c) and wherein the sequences of (a), (b) and (c) must be comprised by the two or more nucleic acids when those nucleic acids are taken together as a group,
    wherein the two or more nucleic acids are capable of homologous recombination with each other to yield a single nucleic acid, and
    wherein the sequence of (c) is split across at least two of the two or more nucleic acids such that each of the at least two of the two or more nucleic acids comprise a sequence encoding a non-functional portion of the recombinase;
    introducing the two or more nucleic acids into the host cell so that recombination into said host cell can take place; and
    recombining the said two or more nucleic acids with each other and with the sequences flanking the target locus so that a contiguous nucleic acid sequence encoding a functional recombinase is inserted at the target locus, said recombinase-encoding sequence being flanked by at least two site-specific recombination sites and the said site-specific recombination sites being flanked by the sequences capable of homologous recombination with sequences flanking the target locus;
    wherein the site-specific recombination sites are lox sites and the recombinase is Cre, the site-specific recombination sites are FRT sites and the recombinase is Flp, the site-specific recombination sites are Vlox sites and the recombinase is VCre, or the site-specific recombination sites are Slox and the recombinase is SCre.

2. The method according to claim 1, wherein the two or more nucleic acids, when taken together, comprise sequences capable of homologous recombination with sequences flanking two or more target loci, so that recombining the said two or more nucleic acids with each other and with the sequences flanking the target loci results in the insertion of at least two site-specific recombination sites at each target loci, wherein:
    a contiguous nucleic acid sequence encoding a functional recombinase is present at least one target locus located between the at least two site-specific recombination sites: and
    the said site-specific recombination sites are flanked by at the sequences capable of homologous recombination with sequences flanking the target locus.

3. The method according to claim 1, wherein two of the at least two nucleic acids each comprise a sequence encoding a non-functional portion of the recombinase such that together they comprise nucleic acid sequence encoding a functional recombinase.

4. The method according to claim 1, which comprises expressing the recombinase so that the sequence located between the site-specific recombination sites is out-recombined.

5. The method according to claim 4, wherein expression of the recombinase is controlled by an inducible promoter.

6. The method according to claim 1, wherein the two or more nucleic acids, taken together, comprise a marker-encoding sequence such that recombination of the two or more nucleic acids results in the said marker gene-encoding sequence being inserted at the target locus or loci such that said marker gene-encoding sequence is located between the at least two of the sequences capable of homologous recombination with sequences flanking the target locus or loci.

7. The method according to claim 2, wherein the two or more nucleic acids, taken together, comprise two or more different marker-encoding sequences such that recombination of the two or more nucleic acids results in a different marker gene-encoding sequence being inserted at each target locus.

8. The method according to claim 6, wherein recombination of the two or more nucleic acids results in the said marker-encoding sequence being inserted at a target locus so that said marker-encoding sequence is located between site-specific recombination sites and may be out-recombined from the target locus on expression of the recombinase.

9. The method according to claim 1, wherein recombination of the nucleic acids with each other and with sequences flanking the target locus is carried out in vivo.

10. The method according to claim 4, wherein out-recombination of the nucleic acid sequence between the site-specific recombination sites is carried out in vivo.

11. The method according to claim 9, wherein the in vivo recombination is carried out in a eukaryotic cell, optionally comprising a mammalian, insect, plant, fungal or algal cell.

12. The method according to claim 11, wherein the fungal cell is a yeast cell, optionally comprising *S. cerevisiae* or *K. lactis*.

13. The method according to claim 11, wherein the fungal cell is a filamentous fungal cell, optionally comprising a cell belonging to a species of an *Aspergillus, Penicillium, Talaromyces* or *Trichoderma* genus.

14. The method according to claim 4, wherein the site-specific recombination sites are such that out-recombination following recombinase expression gives rise to a single mutant site-specific recombination site at the target locus which is not recognized by the recombinase.

15. The method according to claim 1, wherein the target locus comprises a coding sequence which is disrupted and/or partially or fully deleted.

* * * * *